(12) United States Patent
Ha et al.

(10) Patent No.: US 11,020,405 B2
(45) Date of Patent: Jun. 1, 2021

(54) METHOD FOR PREVENTION OR TREATMENT OF DIABETIC COMPLICATIONS

(71) Applicant: KANGWON NATIONAL UNIVERSITY UNIVERSITY-INDUSTRY COOPERATION FOUNDATION, Gangwon-do (KR)

(72) Inventors: Kwon-Soo Ha, Gangwon-do (KR); Yeon-Ju Lee, Gangwon-do (KR); Min-Soo Kim, Gangwon-do (KR)

(73) Assignee: Kangwon National University University-Industry Cooperation Foundation, Gangwon-do (KR)

( * ) Notice: Subject to any disclaimer, the term of this patent is extended or adjusted under 35 U.S.C. 154(b) by 46 days.

(21) Appl. No.: 16/428,073

(22) Filed: May 31, 2019

(65) Prior Publication Data

US 2019/0282586 A1   Sep. 19, 2019

Related U.S. Application Data

(63) Continuation-in-part of application No. 15/864,665, filed on Jan. 8, 2018, now Pat. No. 10,357,498.

(30) Foreign Application Priority Data

Sep. 25, 2017   (KR) .................. 10-2017-0123576

(51) Int. Cl.
*A61K 31/197*   (2006.01)
*A61K 31/5517*  (2006.01)
*A61P 3/10*     (2006.01)

(52) U.S. Cl.
CPC ............ *A61K 31/5517* (2013.01); *A61P 3/10* (2018.01)

(58) Field of Classification Search
CPC .............. A61K 2300/00; A61K 31/197; A61K 31/4465; A61K 38/2013; A61K 39/0008; A61K 39/39; A61K 45/06
See application file for complete search history.

(56) References Cited

U.S. PATENT DOCUMENTS

2013/0251671 A1   9/2013   Kaufman

FOREIGN PATENT DOCUMENTS

KR   10-2003-0084926 A   11/2003
KR   10-2013-0020623 A   2/2013

OTHER PUBLICATIONS

Tian, et al., "Clinically applicable GABA receptor positive allosteric modulators promote β-cell replication", Scientific Reports, 7 pages, Mar. 23, 2017.

*Primary Examiner* — Savitha M Rao
(74) *Attorney, Agent, or Firm* — BakerHostetler

(57) ABSTRACT

Disclosed is a composition for the prevention or treatment of diabetic complications, containing a benzodiazepine-based compound, thereby effectively preventing or treating diseases resulting from hyperglycemia, which is the leading cause of diabetes, especially diseases caused by vascular leakage.

15 Claims, 25 Drawing Sheets

METHOD FOR PREVENTION OR TREATMENT OF DIABETIC COMPLICATIONS

CROSS REFERENCE TO RELATED APPLICATION

This application is a continuation in part application and claims priority to U.S. patent application Ser. No. 15/864,665, filed Jan. 8, 2018, (now U.S. Pat. No. 10,357,498, issued Jul. 23, 2019) which claims the benefit of Korean Patent Application No. KR 10-2017-0123576, filed Sep. 25, 2017, the disclosures of which are hereby incorporated by reference in their entirety into this application.

BACKGROUND OF THE INVENTION

1. Technical Field

The present invention relates to a pharmaceutical composition for the prevention or treatment of diabetic complications, containing a benzodiazepine-based compound.

2. Description of the Related Art

Diabetes mellitus is a metabolic disease of chronic hyperglycemia that is associated with progressive damage to and dysfunction of blood vessels, resulting in two types of organ-specific diseases: micro- and macrovascular complications. The pathogenesis of diabetic complications is multifactorial; however, the common recipient of injury is the vascular endothelium, which shows vascular inflammation, a pro-thrombotic state, and impaired vascular functions such as hyperpermeability. Diabetic retinopathy (DR) is a serious long-term microvascular complication and the leading cause of blindness in adults. Clinically, DR progresses from non-proliferative to proliferative disease stages. In non-proliferative DR, sustained hyperglycemia induces retinal blood vessel damage such as pericyte loss, microaneurysms, and vascular leakage. In proliferative DR, neovascularization starts as a result of hypoxia and macular edema and contributes to visual impairment. Thus, the prevention of vasculature alterations and vascular leakage in the early stages is important for preventing DR.

Retinal vascular permeability in the early stages of DR is predominantly caused by the pathological release of vascular endothelial growth factor (VEGF) in the retinas of diabetic patients. VEGF induces stress fiber formation and vascular endothelial (VE)-cadherin disruption, which result in adherens junction disassembly and vascular leakage in diabetic retinas. Recently, the present inventors demonstrated that reactive oxygen species (ROS)-mediated activation of transglutaminase (TGase) 2 plays a key role in VEGF-induced retinal vascular leakage in diabetic mice. Although various drugs against VEGF, oxidative stress, and inflammation have been evaluated for the treatment of DR, there is strong demand for longer-acting and non-invasive therapies with minimal complications for the prevention and treatment of diabetic retinal vascular disease.

In this regard, Korean Patent Application Publication No. 10-2013-0020623 discloses a composition for the prevention or treatment of diabetic complications, containing a *Quamoclit angulata* extract, but is problematic because the above composition merely exhibits the effects of prevention or treatment of diabetic complications through blood glucose reduction and urinary protein inhibition and does not act on the signal transmission process of VEGF, which is the main cause of diabetic complications.

CITATION LIST

Patent Literature

Korean Patent Application Publication No. 10-2013-0020623

SUMMARY OF THE INVENTION

Accordingly, the present invention is intended to provide a pharmaceutical composition for the effective prevention or treatment of diabetic complications, such as a disease due to vascular leakage caused by hyperglycemia, for example, diabetic retinopathy.

Therefore, the present invention provides a pharmaceutical composition and a method for the prevention or treatment of diabetic complications, comprising a benzodiazepine-based compound.

In the present invention, the benzodiazepine-based compound may include at least one selected from among midazolam, alprazolam, lorazepam, diazepam, estazolam, flurazepam, and triazolam.

In the present invention, the diabetic complications may include at least one selected from among diabetic retinopathy, diabetic cardiovascular disease, diabetic stroke, diabetic kidney disease, diabetic lung disease, diabetic peripheral neuropathy and diabetic cancer metastasis.

In the present invention, the diabetic complications may be caused by vascular leakage.

In the present invention, the vascular leakage may be caused by VEGF (Vascular Endothelial Growth Factor).

In the present invention, the benzodiazepine-based compound may inhibit intracellular $Ca^{2+}$ elevation induced by the VEGF.

In the present invention, the benzodiazepine-based compound may inhibit at least one of reactive oxygen species (ROS) generation, TGase (transglutaminase) activation and adherens junction disruption, which are induced by the intracellular $Ca^{2+}$ elevation.

In the present invention, the benzodiazepine-based compound may act through a $GABA_A$ (γ-aminobutyric acid type A) receptor.

In the present invention, the pharmaceutical composition for the prevention or treatment of diabetic complications may be used for at least one of ocular administration, intravitreal injection, vascular injection, intraperitoneal injection, subcutaneous injection, nasal aspiration and oral administration.

According to the present invention, a pharmaceutical composition for the prevention or treatment of diabetic complications contains a benzodiazepine-based compound to thereby effectively prevent and treat diseases resulting from hyperglycemia, which is the leading cause of diabetes. Specifically, hyperglycemia induces an increase in VEGF expression, and VEGF induces intracellular $Ca^{2+}$ elevation, ROS generation, TGase activation, and adherens junction disruption, resulting in diabetic complications. The pharmaceutical composition for the prevention or treatment of diabetic complications according to the present invention can effectively prevent or treat diabetic complications by acting on the pathogenesis of VEGF that induces intracellular $Ca^{2+}$ elevation and the like.

DESCRIPTION OF SPECIFIC EMBODIMENTS

The present invention addresses a pharmaceutical composition for the prevention or treatment of diabetic complications, comprising a benzodiazepine-based compound, or a therapeutic method using the same.

The present inventors have experimentally ascertained that the benzodiazepine-based compound is able to inhibit intracellular $Ca^{2+}$ elevation induced by VEGF, and also to inhibit ROS generation, TGase activation or adherens junction disruption induced by the intracellular $Ca^{2+}$ elevation, thereby enabling the prevention, treatment or amelioration of diabetic complications caused by vascular leakage, which culminates in the present invention.

Herein, diabetic complications may include, for example, diabetic retinopathy, but are not limited thereto, and diabetic complications may include all complications caused by vascular leakage, such as diabetic stroke, diabetic cardiovascular disease, diabetic kidney disease, diabetic lung disease, diabetic peripheral neuropathy and diabetic cancer metastasis.

Herein, the benzodiazepine-based compound includes at least one selected from among midazolam, alprazolam, lorazepam, diazepam, estazolam, flurazepam and triazolam. Midazolam is preferably used.

Figure 1:
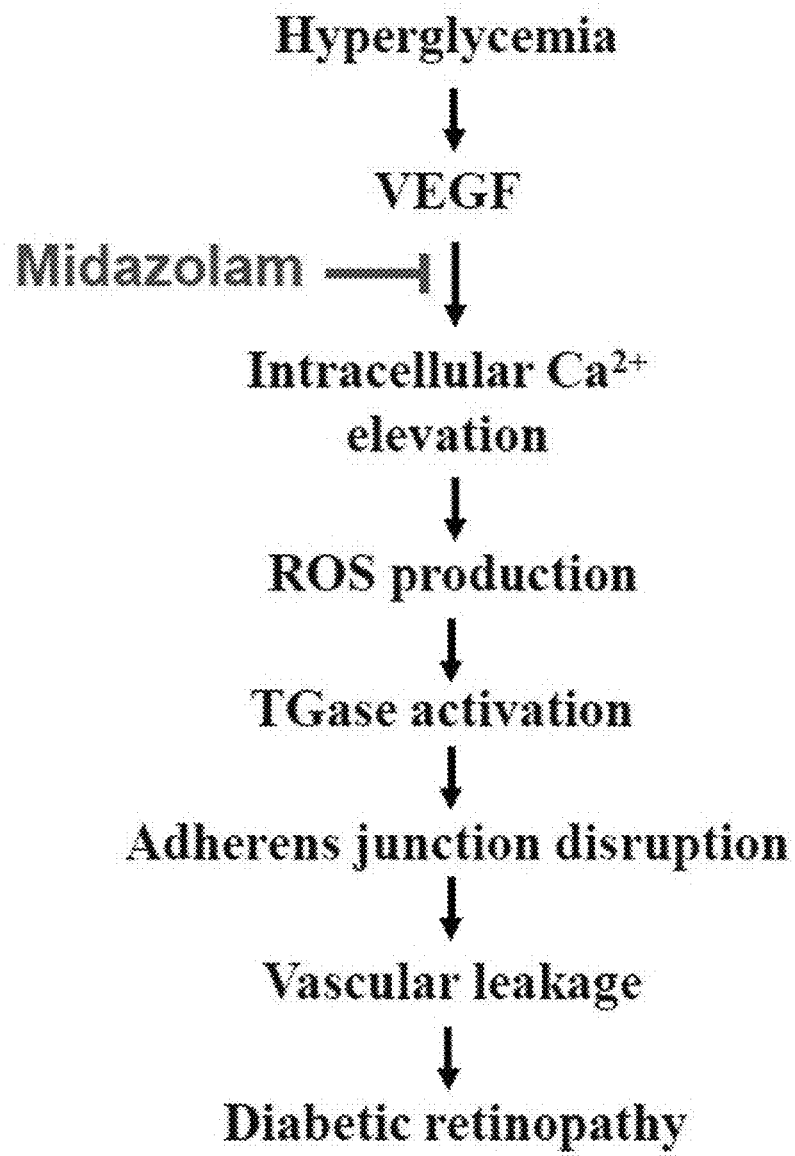
FIG. 1 shows the pathogenesis of diabetic complications and the mechanism of action of a pharmaceutical composition for the prevention or treatment of diabetic complications according to the present invention.

With reference to FIG. 1, the pathogenesis of diabetic complications due to hyperglycemia, which is the leading cause of diabetes, and the mechanism of action of the pharmaceutical composition for the prevention or treatment of diabetic complications according to the present invention on the pathogenesis of diabetic complications so as to prevent or treat diabetic complications are described.

Hyperglycemia may induce an increase in VEGF expression. When in-vivo VEGF expression increases due to hyperglycemia, intracellular $Ca^{2+}$ elevation may occur. When the intracellular $Ca^{2+}$ elevation occurs in this way, ROS production and TGase activation may be increased and adherens junction disruption may take place, thus causing vascular leakage. Diabetic complications, for example, diabetic retinopathy, may be caused by vascular leakage.

The pharmaceutical composition for the prevention or treatment of diabetic complications according to the present invention contains a benzodiazepine-based compound, and the benzodiazepine-based compound, for example, midazolam, may act on the pathogenesis in which intracellular $Ca^{2+}$ elevation is induced by an increase in VEGF expression, thus suppressing intracellular $Ca_{2+}$ elevation. Thereby, the pharmaceutical composition for the prevention or treatment of diabetic complications according to the present invention is effective at preventing or treating diabetic complications due to vascular leakage caused by intracellular $Ca^{2+}$ elevation.

The pharmaceutical composition for the prevention or treatment of diabetic complications according to the present invention may be administered in an "effective amount" or a "pharmaceutically effective amount". The term "effective amount" or "pharmaceutically effective amount" refers to an amount sufficient to exhibit the preventive or therapeutic effect on diabetic complications and to an amount that does not cause side effects or serious or excessive immune responses, and the effective dose level may vary depending on a variety of factors, including the disorder to be treated, the severity of the disorder, the activity of a particular compound, the route of administration, the rate of elimination, the duration of treatment, the drugs used in combination or concurrently therewith, the subject's age, weight, gender, dietary habits, general health status, and factors known in the medical and pharmaceutical arts. Various general factors considered in determining the "effective amount" or "pharmaceutically effective amount" are known to those skilled in the art.

Preferably, the pharmaceutical composition for the prevention or treatment of diabetic complications according to the present invention may be used for at least one selected from among ocular administration, intravitreal injection, vascular injection, intraperitoneal injection, subcutaneous injection, nasal inhalation and oral administration.

The pharmaceutical composition for the prevention or treatment of diabetic complications according to the present invention may be appropriately administered so as to be suitable for the type of disease and the weight of a subject. Preferably, in order to prevent or treat diabetic retinopathy of a human, when the pharmaceutical composition for the prevention or treatment of diabetic complications, containing midazolam, is administered in the form of ocular injection, a single dose thereof may be about 6.66 μg to 6.66 mg. Alternatively, in order to prevent or treat diabetic retinopathy of a human, when the pharmaceutical composition for the prevention or treatment of diabetic complications, containing midazolam, is administered in the form of ocular administration, vascular injection, intraperitoneal injection, subcutaneous injection, nasal aspiration or oral administration, the administration concentration may be about 0.3 nM to 600 nM. The above administration method and concentration are not limited to diabetic retinopathy, and may be applied to at least one selected from among diabetic cardiovascular disease, diabetic stroke, diabetic kidney disease, diabetic lung disease, diabetic peripheral neuropathy and diabetic cancer metastasis.

A better understanding of the present invention will be given through the following Examples and Test Examples, which are merely set forth to illustrate the present invention, and the present invention is not limited to the following Examples and Test Examples but may be variously modified and altered.

Test Example 1. Cell Culture

Purchased from Applied Cell Biology Research Institute (Cell Systems, Kirkland, Wash.), human retinal endothelial cells (HRECs) were cultured in an M19 medium, containing 20% FBS, 3 ng/mL bFGF, 5 U/mL heparin, 100 U/mL penicillin and 100 mg/mL streptomycin, in a 2% gelatin-coated plate.

Before the following Test Examples 2 to 7, the HRECs were cultured for 6 hr in a medium containing 1% FBS and an antibiotic agent, thus preparing HRECs of Test Example 1.

Test Example 2. Analysis of Intracellular $Ca^{2+}$

Figure 2A:
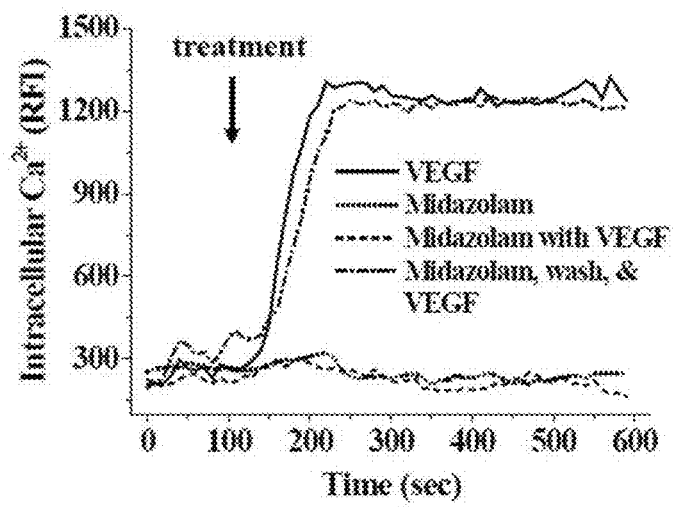
FIGS. 2A and 2B show the results of measurement of changes in intracellular $Ca^{2+}$ concentration in Test Example 2 of the present invention.

With reference to FIG. 2A, the HRECs of Test Example 1 were subjected to the respective treatments below, stained with 2 μM Fluo4-AM at 37° C. for 30 min and then measured at time intervals of 10 sec using confocal microscopy (FV-300, Olympus, Tokyo, Japan).

i) Treatment with 10 ng/ml VEGF (VEGF)
ii) Treatment with 20 μM midazolam (Midazolam)
iii) Treatment with 10 ng/ml VEGF and 20 μM midazolam (Midazolam with VEGF)
iv) Treatment with 20 μM midazolam, culture for 30 min, washing with serum-free medium, and treatment with 10 ng/ml VEGF (Midazolam, wash, & VEGF)

Based on the results of measurement, intracellular $Ca^{2+}$ elevation was caused in the HRECs subjected to i) treatment with VEGF (VEGF) and the HRECs subjected to iv) treatment with midazolam, washing and treatment with VEGF (Midazolam, wash, & VEGF), and there were no significant changes in intracellular $Ca^{2+}$ in the HRECs subjected to ii) treatment with midazolam (Midazolam) and the HRECs subjected to iii) treatment with VEGF and midazolam (Midazolam with VEGF).

Accordingly, it can be confirmed that VEGF induced intracellular $Ca^{2+}$ elevation and midazolam inhibited intracellular $Ca^{2+}$ elevation. Furthermore, through the intracellular $Ca^{2+}$ elevation in the HRECs subjected to iv) treatment with midazolam, washing and treatment with VEGF (Midazolam, wash, & VEGF), the effect of midazolam on the inhibition of $Ca^{2+}$ elevation was found to disappear after washing, even upon treatment with midazolam.

Figure 2B:
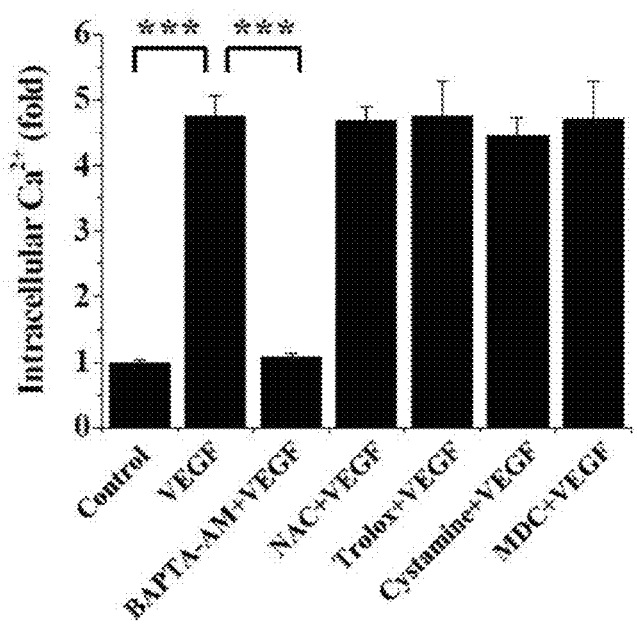

With reference to FIG. 2B, the HRECs of Test Example 1 were subjected to the respective treatments below, cultured for 30 min, stained with 2 μM Fluo4-AM at 37° C. for 30 min and then measured at time intervals of 10 sec using confocal microscopy.

i) Non-treatment (Control)
ii) Treatment with 10 ng/mL VEGF (VEGF)
iii) Treatment with 5 μM BAPTA-AM and 10 ng/mL VEGF (BAPTA-AM+VEGF)
iv) Treatment with 1 mM NAC and 10 ng/mL VEGF (NAC+VEGF)
v) Treatment with 0.5 μM Trolox and 10 ng/mL VEGF (Trolox+VEGF)
vi) Treatment with 50 μM cystamine and 10 ng/mL VEGF (cystamine+VEGF)
vii) Treatment with 20 μM MDC and 10 ng/mL VEGF (MDC+VEGF)

BAPTA-AM was a calcium-ion chelating agent, NAC and Trolox were ROS scavengers, and cystamine and MDC were TGase inhibitors.

Based on the results of measurement, compared to the i) non-treated HRECs (Control), there were no significant changes in intracellular $Ca^{2+}$ in the HRECs subjected to iii) treatment with BAPTA-AM and VEGF (BAPTA-AM+VEGF), and intracellular $Ca^{2+}$ elevation was caused in the HRECs subjected to ii) treatment with VEGF (VEGF), the HRECs subjected to iv) treatment with NAC and VEGF (NAC+VEGF), the HRECs subjected to v) treatment with Trolox and VEGF (Trolox+VEGF), the HRECs subjected to vi) treatment with cystamine and VEGF (cystamine+VEGF), and the HRECs subjected to vii) treatment with MDC and VEGF (MDC+VEGF).

As shown in FIGS. 2A and 2B, midazolam exhibited substantially the same effect of inhibiting intracellular $Ca^{2+}$ elevation as the calcium-ion chelating agent BAPTA-AM.

Test Example 3. Analysis of ROS of Cells

Figure 3A:
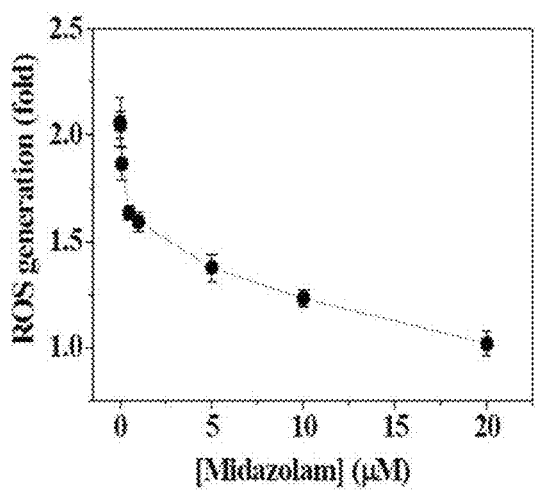
FIGS. 3A and 3B show the results of measurement of changes in ROS concentration in Test Example 3 of the present invention.

With reference to FIG. 3A, the HRECs of Test Example 1 were treated with 0 to 20 μM midazolam, cultured for 30 min, treated with 10 ng/mL VEGF and 10 μM H2DCFDA (Molecular Probes, Eugene, Oreg.), stained for 10 min in a phenol-red-free low-serum medium, and then measured using confocal microscopy to thus determine the fluorescence intensity of single cells.

Based on the results of measurement, ROS concentration was decreased with an increase in the concentration of midazolam used for the HRECs.

Figure 3B:
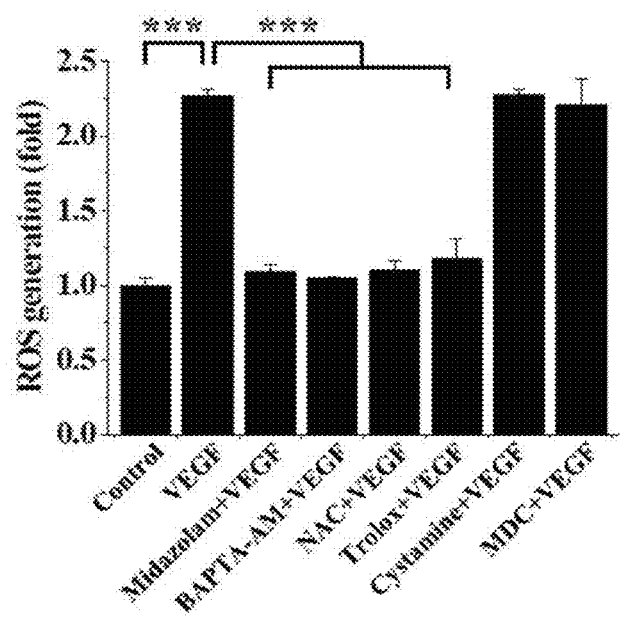

With reference to FIG. 3B, the HRECs of Test Example 1 were subjected to the respective treatments below and cultured for 30 min. Upon treatment with 10 ng/mL VEGF, treatment with 10 µM H2DCFDA was performed therewith, or alternatively, treatment with 10 µM H2DCFDA was performed alone, followed by staining for 10 min in a phenol-red-free low-serum medium and then measurement via confocal microscopy to thus determine the fluorescence intensity of single cells.

i) Non-treatment (Control)
ii) Treatment with 10 ng/mL VEGF (VEGF)
iii) Treatment with 20 µM midazolam and 10 ng/mL VEGF (Midazolam+VEGF)
iv) Treatment with 5 µM BAPTA-AM and 10 ng/mL VEGF (BAPTA-AM+VEGF)
v) Treatment with 1 mM NAC and 10 ng/mL VEGF (NAC+VEGF)
vi) Treatment with 0.5 µM Trolox and 10 ng/mL VEGF (Trolox+VEGF)
vii) Treatment with 50 µM cystamine and 10 ng/mL VEGF (cystamine+VEGF)
viii) Treatment with 20 µM MDC and 10 ng/mL VEGF (MDC+VEGF)

BAPTA-AM was a calcium-ion chelating agent, NAC and Trolox were ROS scavengers, and cystamine and MDC were TGase inhibitors.

Based on the results of measurement, compared to the i) non-treated HRECs (Control), no significant ROS concentration increase was observed in the HRECs subjected to iii) treatment with midazolam and VEGF (Midazolam+VEGF), the HRECs subjected to iv) treatment with BAPTA-AM and VEGF (BAPTA-AM+VEGF), the HRECs subjected to v) treatment with NAC and VEGF (NAC+VEGF) and the HRECs subjected to vi) treatment with Trolox and VEGF (Trolox+VEGF), whereas ROS concentration was increased in the HRECs subjected to ii) treatment with VEGF (VEGF), the HRECs subjected to vii) treatment with cystamine and VEGF (cystamine+VEGF), and the HRECs subjected to viii) treatment with MDC and VEGF (MDC+VEGF).

Thus, as shown in FIGS. 3A and 3B, midazolam exhibited substantially the same effect of inhibiting an increase in ROS concentration as the ROS scavengers NAC and Trolox. Furthermore, the use of midazolam, having substantially the same effect of inhibiting ROS increase as NAC and Trolox, resulted in inhibited intracellular $Ca^{2+}$ elevation to thus suppress an increase in ROS.

Test Example 4. Analysis of TGase Activity of Cells

Figure 4A:
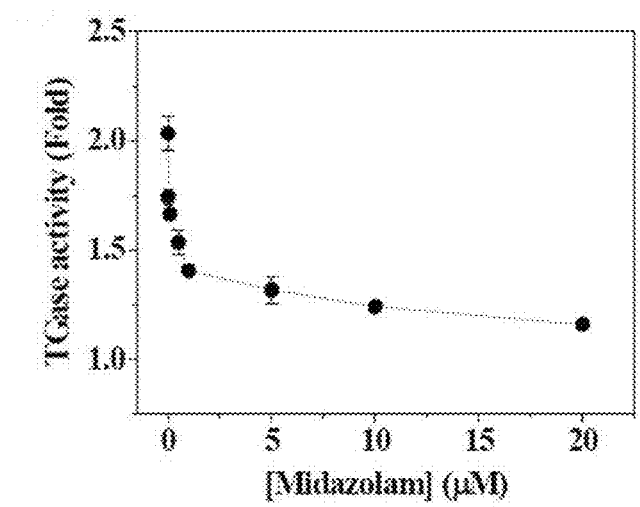
FIGS. 4A and 4B show the results of measurement of changes in TGase activity in Test Example 4 of the present invention.

With reference to FIG. 4A, the HRECs of Test Example 1 were treated with 0 to 20 µM midazolam, cultured for 2 hr, treated with 10 ng/mL VEGF, incubated for 2 hr, treated with 1 mM 5-(biotinamido)pentylamine, incubated for 1 hr, fixed with 3.7% formaldehyde, treated with 0.2% triton X-100, treated with a blocking solution containing 138 mM NaCl, 0.1% Tween 20 and 2% BSA dissolved in a 20 mM Tris (pH 7.6) buffer, incubated for 30 min, incubated for 1 hr with FITC-conjugated streptavidin (1:200, v/v), and then measured using confocal microscopy to thus determine the fluorescence intensity of single cells.

Based on the results of measurement, TGase activity was decreased with an increase in the concentration of midazolam used for the HRECs.

Figure 4B:
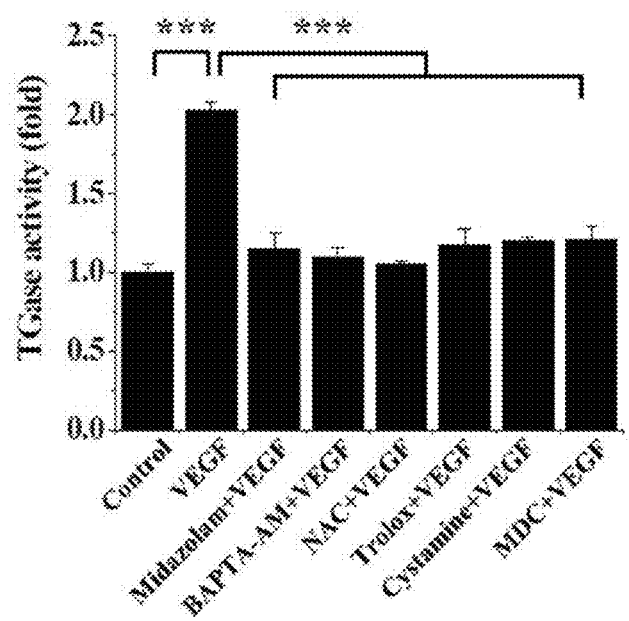

With reference to FIG. 4B, the HRECs of Test Example 1 were subjected to the respective treatments below and cultured for 30 min. Here, treatment with 10 ng/mL VEGF was performed for 2 hr. Thereafter, the HRECs were treated with 1 mM 5-(biotinamido)pentylamine, incubated for 1 hr, fixed with 3.7% formaldehyde, treated with 0.2% triton X-100, treated with a blocking solution containing 138 mM NaCl, 0.1% Tween 20 and 2% BSA dissolved in a 20 mM Tris (pH 7.6) buffer, incubated for 30 min, incubated for 1 hr with FITC-conjugated streptavidin (1:200, v/v), and then measured using confocal microscopy to thus determine the fluorescence intensity of single cells.

i) Non-treatment (Control)
ii) Treatment with 10 ng/mL VEGF (VEGF)
iii) Treatment with 20 µM midazolam and 10 ng/mL VEGF (Midazolam+VEGF)
iv) Treatment with 5 µM BAPTA-AM and 10 ng/mL VEGF (BAPTA-AM+VEGF)
v) Treatment with 1 mM NAC and 10 ng/mL VEGF (NAC+VEGF)
vi) Treatment with 0.5 µM Trolox and 10 ng/mL VEGF (Trolox+VEGF)
vii) Treatment with 50 µM cystamine and 10 ng/mL VEGF (cystamine+VEGF)
viii) Treatment with 20 µM MDC and 10 ng/mL VEGF (MDC+VEGF)

BAPTA-AM was a calcium-ion chelating agent, NAC and Trolox were ROS scavengers, and cystamine and MDC were TGase inhibitors.

Based on the results of measurement, compared to the i) non-treated HRECs (Control), no significant TGase activity increase was observed in any of the test groups, excluding the HRECs subjected to ii) treatment with VEGF (VEGF).

As shown in FIGS. 4A and 4B, midazolam exhibited substantially the same effect of inhibiting TGase activity as the TGase inhibitors cystamine and MDC. Furthermore, the use of midazolam, having substantially the same effect of inhibiting TGase activity as cystamine and MDC, resulted in inhibited intracellular $Ca^{2+}$ elevation and ROS increase to thus suppress the TGase activation.

Test Example 5. Analysis of Adherens Junction (VE-Cadherin)

Figure 5:
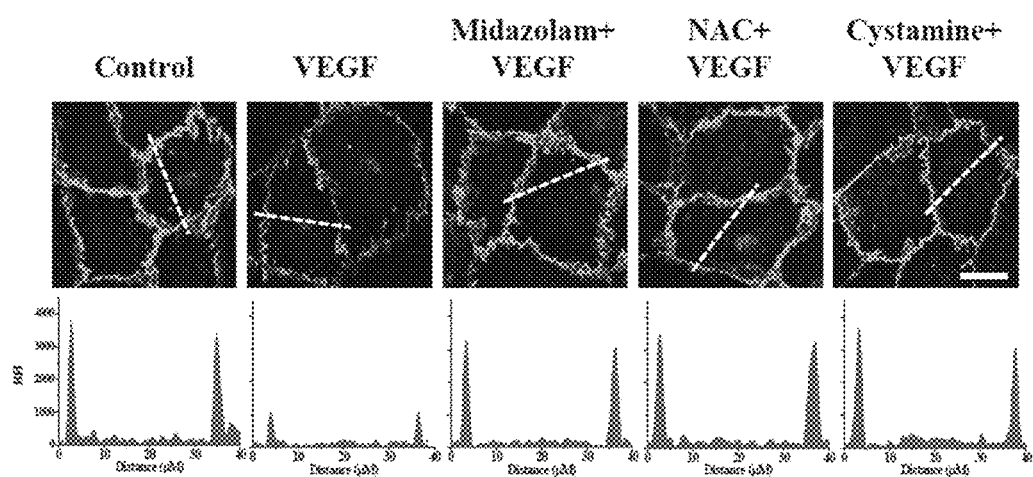
FIGS. 5 and 6 show the results of measurement of changes in VE-cadherin in Test Example 5 of the present invention.
Figure 6:
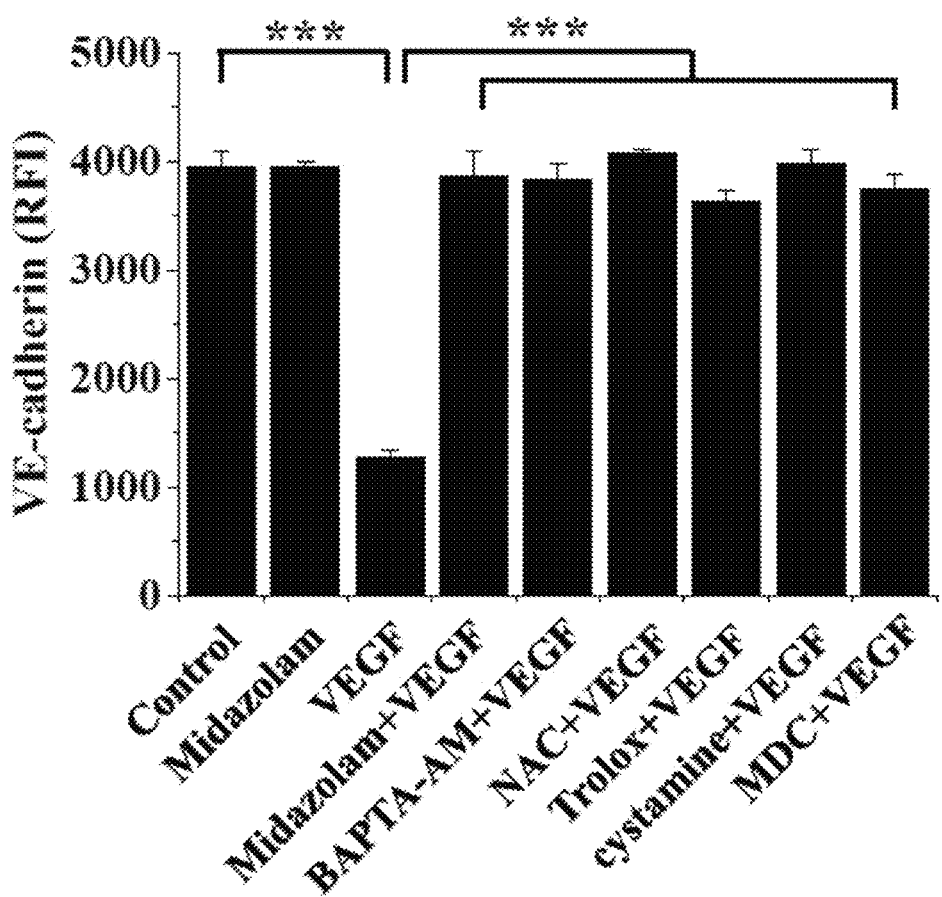

The HRECs of Test Example 1 were subjected to the respective treatments below and cultured for 30 min. Here, treatment with 10 ng/mL VEGF was performed for 90 min. Thereafter, the HRECs were treated with 1 mM 5-(biotinamido)pentylamine, incubated for 1 hr, fixed with 3.7% formaldehyde, treated with 0.2% triton X-100, treated with a blocking solution containing 138 mM NaCl, 0.1% Tween 20 and 2% BSA dissolved in a 20 mM Tris (pH 7.6) buffer, incubated for 30 min, incubated with a monoclonal VE-cadherin antibody (1:200; Santa Cruz Biotechnology) for 12 hr or more (overnight), incubated with a FITC-conjugated goat anti-mouse antibody (1:200; Sigma-Aldrich), and then measured using confocal microscopy. Some (the following i), iii), iv), vi), ix)) of the results are shown in FIG. 5 and the VE-cadherin concentrations in the portions represented by the dotted lines in FIG. 5 are shown in FIG. 6. With reference to FIG. 6, 10 randomly selected cells were measured to determine the fluorescence intensity of single cells and thus quantify VE-cadherin.

i) Non-treatment (Control)
ii) Treatment with 20 µM midazolam (Midazolam)
iii) Treatment with 10 ng/mL VEGF (VEGF)
iv) Treatment with 20 µM midazolam and 10 ng/mL VEGF (Midazolam+VEGF)
v) Treatment with 5 µM BAPTA-AM and 10 ng/mL VEGF (BAPTA-AM+VEGF)
vi) Treatment with 1 mM NAC and 10 ng/mL VEGF (NAC+VEGF)
vii) Treatment with 0.5 µM Trolox and 10 ng/mL VEGF (Trolox+VEGF)
viii) Treatment with 50 µM cystamine and 10 ng/mL VEGF (cystamine+VEGF)
ix) Treatment with 20 µM MDC and 10 ng/mL VEGF (MDC+VEGF)

BAPTA-AM was a calcium-ion chelating agent, NAC and Trolox were ROS scavengers, and cystamine and MDC were TGase inhibitors.

VE-cadherin, which is a protein that mediates adherens junction, was analyzed to evaluate adherens junction.

Based on the results of measurement, compared to the i) non-treated HRECs (Control), high VE-cadherin concentration was measured in all of the test groups, excluding the HRECs subjected to iii) treatment with VEGF (VEGF), from which adherens junction disruption was confirmed not to occur.

Thus, as shown in FIGS. 5 and 6, midazolam exhibited the effect of preventing the adherens junction disruption due to VEGF.

Furthermore, the effect of preventing the adherens junction disruption was also observed in BAPTA-AM, serving as the calcium-ion chelating agent, NAC and Trolox, serving as the ROS scavengers, and cystamine and MDC, serving as the TGase inhibitors. Thereby, when intracellular $Ca^{2+}$ elevation, ROS production and TGase activation induced by VEGF are inhibited, the disruption of adherens junction can be concluded to be prevented.

Test Example 6. Analysis of Cell Permeability

Figure 7:
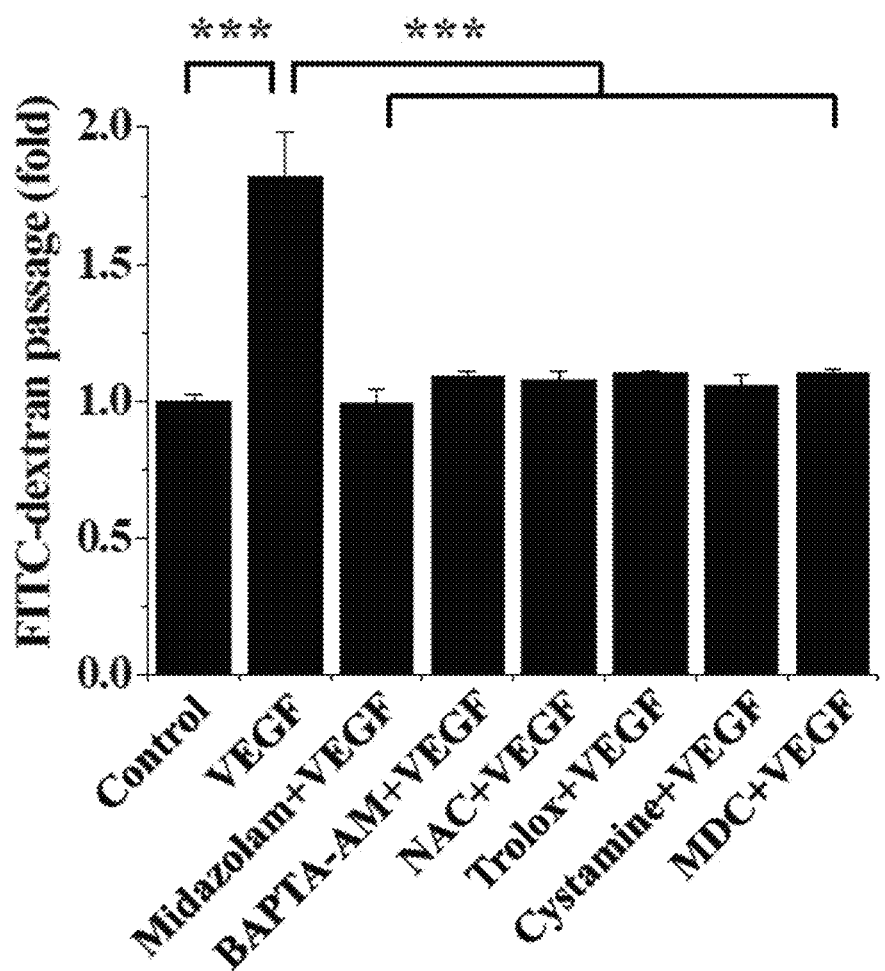
FIG. 7 shows the results of measurement of cell permeability in Test Example 6 of the present invention.

The HRECs were cultured (e.g. about 5 days) until the cell confluence thereof reached an appropriate level on gelatin-coated 0.4 µm polycarbonate membranes of Transwell Permeable Supports (Costar, Corning, N.Y.), followed by the respective treatments below and culture for 30 min. Here, treatment with 10 ng/mL VEGF was performed for 90 min. Thereafter, the HRECs were treated with 1 mg/mL 40 kDa FITC-dextran (Sigma-Aldrich), incubated for 60 min, after which the amount of FITC-dextran that was diffused into the lower chamber through the endothelial monolayer of HERCs was measured using a microplate spectrofluorometer (Molecular Devices, Sunnyvale, Calif.). The results are shown in FIG. 7.

i) Non-treatment (Control)
ii) Treatment with 10 ng/mL VEGF (VEGF)
iii) Treatment with 20 µM midazolam and 10 ng/mL VEGF (Midazolam+VEGF)
iv) Treatment with 5 µM BAPTA-AM and 10 ng/mL VEGF (BAPTA-AM+VEGF)
v) Treatment with 1 mM NAC and 10 ng/mL VEGF (NAC+VEGF)
vi) Treatment with 0.5 µM Trolox and 10 ng/mL VEGF (Trolox+VEGF)
vii) Treatment with 50 µM cystamine and 10 ng/mL VEGF (cystamine+VEGF)
viii) Treatment with 20 µM MDC and 10 ng/mL VEGF (MDC+VEGF)

BAPTA-AM was a calcium-ion chelating agent, NAC and Trolox were ROS scavengers, and cystamine and MDC were TGase inhibitors.

Based on the results of measurement, compared to the i) non-treated HRECs (Control), fluorescence intensity by the FITC-dextran was measured to be low in all of the test groups, excluding the HRECs subjected to iii) treatment with VEGF (VEGF), whereby the FITC-dextran could not be diffused up to the lower chamber.

That is, midazolam prevented the adherens junction disruption due to VEGF and thus FITC-dextran was not diffused.

Accordingly, midazolam exhibited the effect of preventing the adherens junction disruption due to VEGF. Furthermore, the effect of preventing the adherens junction disruption was also observed in BAPTA-AM, serving as the calcium-ion chelating agent, NAC and Trolox, serving as the ROS scavengers, and cystamine and MDC, serving as the TGase inhibitors. Thereby, when intracellular $Ca^{2+}$ elevation, ROS production and TGase activation induced by VEGF are inhibited, the disruption of adherens junction can be concluded to be prevented.

Test Example 7. Analysis of Adherens Junction (β-Catenin)

Figure 8:
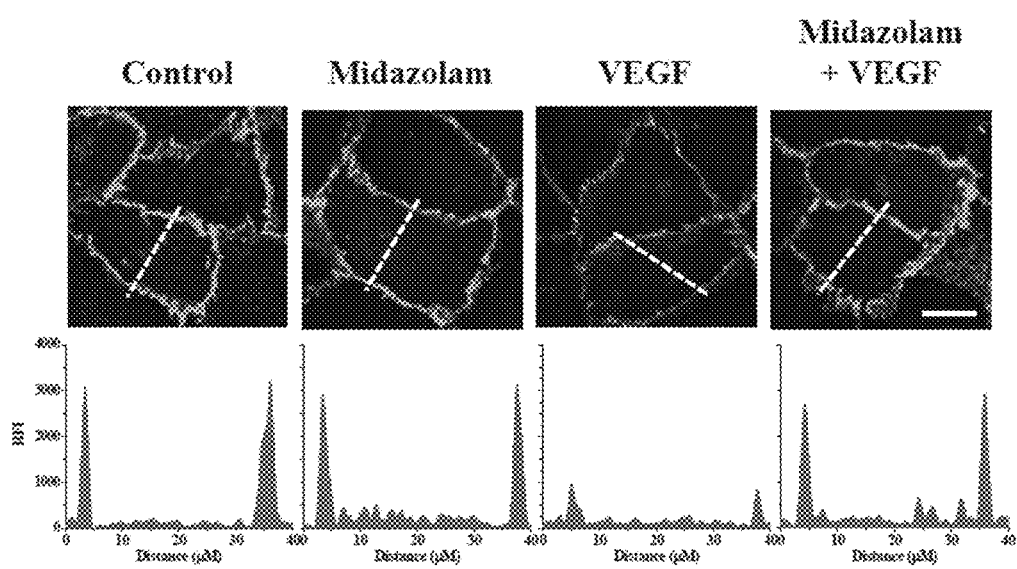
FIGS. 8 and 9 show the results of measurement of changes in β-catenin in Test Example 7 of the present invention.
Figure 9:
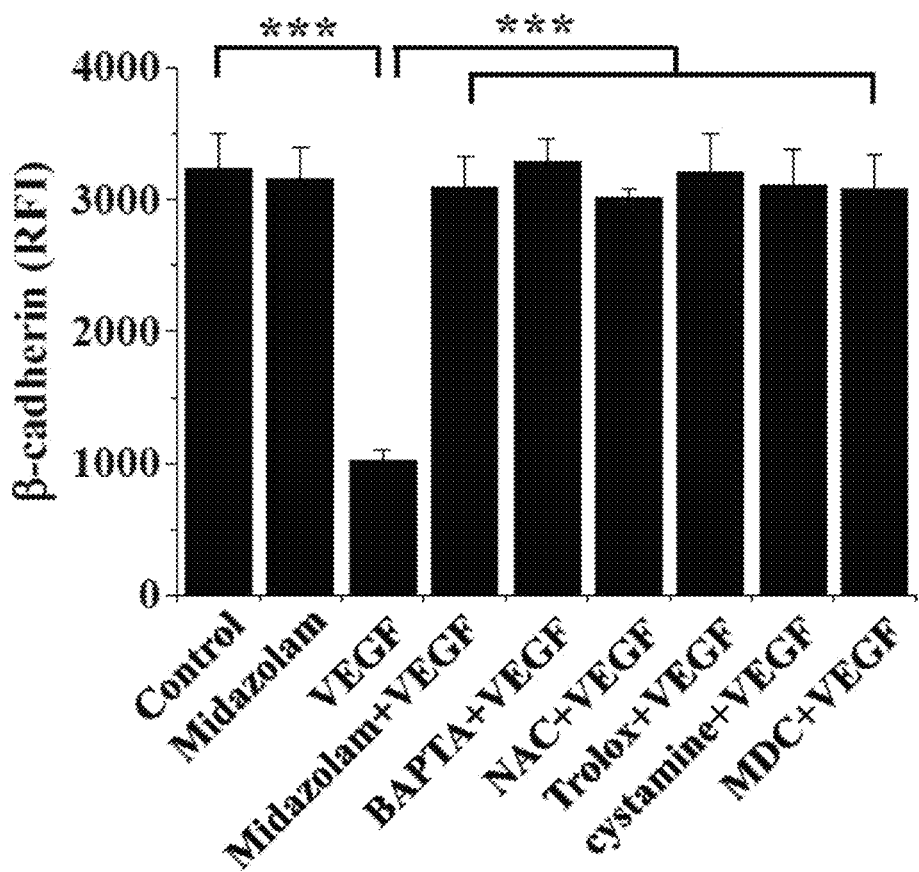

The HRECs of Test Example 1 were subjected to the respective treatments below and cultured for 30 min. Here, treatment with 10 ng/mL VEGF was performed for 90 min. Thereafter, the HRECs were treated with 1 mM 5-(biotinamido)pentylamine, incubated for 1 hr, fixed with 3.7% formaldehyde, treated with 0.2% triton X-100, treated with a blocking solution containing 138 mM NaCl, 0.1% Tween 20 and 2% BSA dissolved in a 20 mM Tris (pH 7.6) buffer, incubated for 30 min, incubated with a monoclonal β-catenin antibody (1:200; Santa Cruz Biotechnology) for 12 hr or more, incubated with a FITC-conjugated goat anti-mouse antibody, and measured using confocal microscopy. Some (the following i), ii), iii), iv)) of the results are shown in FIG. 8, and the β-catenin concentrations in the portions represented by the dotted lines in FIG. 8 are shown in FIG. 9. With reference to FIG. 9, 10 randomly selected cells were measured to determine the fluorescence intensity of single cells and thus quantify β-catenin.

i) Non-treatment (Control)
ii) Treatment with 20 µM midazolam (Midazolam)
iii) Treatment with 10 ng/mL VEGF (VEGF)
iv) Treatment with 20 µM midazolam and 10 ng/mL VEGF (Midazolam+VEGF)
v) Treatment with 5 µM BAPTA-AM and 10 ng/mL VEGF (BAPTA-AM+VEGF)
vi) Treatment with 1 mM NAC and 10 ng/mL VEGF (NAC+VEGF)
vii) Treatment with 0.5 µM Trolox and 10 ng/mL VEGF (Trolox+VEGF)
viii) Treatment with 50 µM cystamine and 10 ng/mL VEGF (cystamine+VEGF)
ix) Treatment with 20 µM MDC and 10 ng/mL VEGF (MDC+VEGF)

BAPTA-AM was a calcium-ion chelating agent, NAC and Trolox were ROS scavengers, and cystamine and MDC were TGase inhibitors.

β-catenin, which is a protein that mediates adherens junction like VE-cadherin, was analyzed to evaluate adherens junction.

Based on the results of measurement, compared to the i) non-treated HRECs (Control), β-catenin concentration was measured to be high in all of the test groups, excluding the HRECs subjected to iii) treatment with VEGF (VEGF), from which adherens junction disruption was confirmed not to occur.

With reference to FIGS. 8 and 9, midazolam exhibited the effect of preventing the adherens junction disruption due to VEGF.

Furthermore, the effect of preventing the adherens junction disruption was also observed in BAPTA-AM, serving as the calcium-ion chelating agent, NAC and Trolox, serving as the ROS scavengers, and cystamine and MDC, serving as the TGase inhibitors. Thereby, when intracellular $Ca^{2+}$ elevation, ROS production and TGase activation induced by VEGF are inhibited, the disruption of adherens junction can be concluded to be prevented.

Figure 10A:
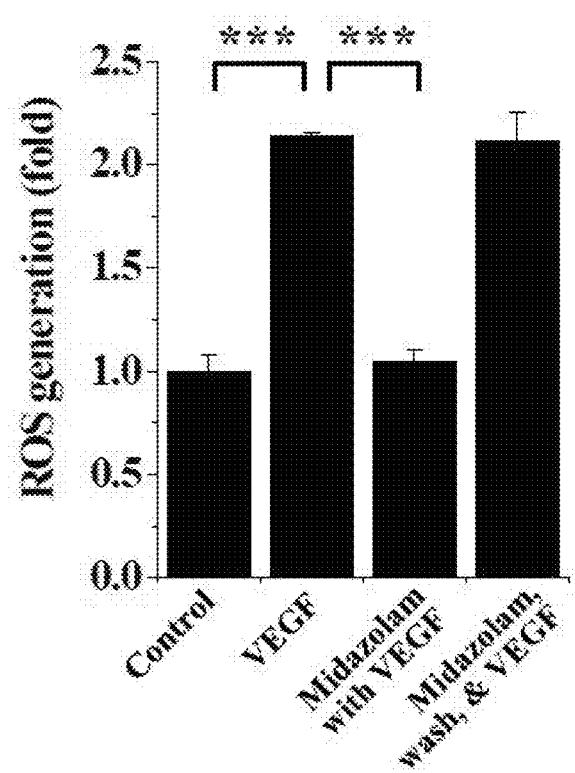
FIGS. 10A and 10B show the effects of flumazenil, serving as a $GABA_A$ receptor antagonist, and PK11195, serving as a TSPO receptor antagonist, on ROS increased by VEGF in Test Example 8 of the present invention.

Test Example 8. Identification of Receptor of Midazolam Through ROS Concentration Analysis With reference to FIG. 10A, the HRECs of Test Example 1 were subjected to the respective treatments below, cultured for 10 min, treated with 10 μM H2DCFDA, stained for 10 min in a phenol-red-free low-serum medium, and measured using confocal microscopy to thus determine the fluorescence intensity of single cells.

i) Non-treatment (Control)
ii) Treatment with 10 ng/ml VEGF (VEGF)
iii) Treatment with 20 μM midazolam, culture for 10 min and treatment with 10 ng/ml VEGF (Midazolam with VEGF)
iv) Treatment with 20 μM midazolam, culture for 30 min, washing with serum-free medium and treatment with 10 ng/ml VEGF (Midazolam, wash, & VEGF)

Based on the results of measurement, compared to the i) non-treated HRECs (Control), no significant ROS concentration increase was observed in the HRECs subjected to iii) treatment with midazolam and VEGF (Midazolam+VEGF), and ROS concentration was increased in the HRECs subjected to ii) treatment with VEGF (VEGF) and the HRECs subjected to iv) treatment with midazolam, washing and treatment with VEGF (Midazolam, wash, & VEGF).

As will be described below, flumazenil was used as a $GABA_A$ receptor antagonist and PK11195 was used as a TSOP receptor antagonist.

Figure 10B:
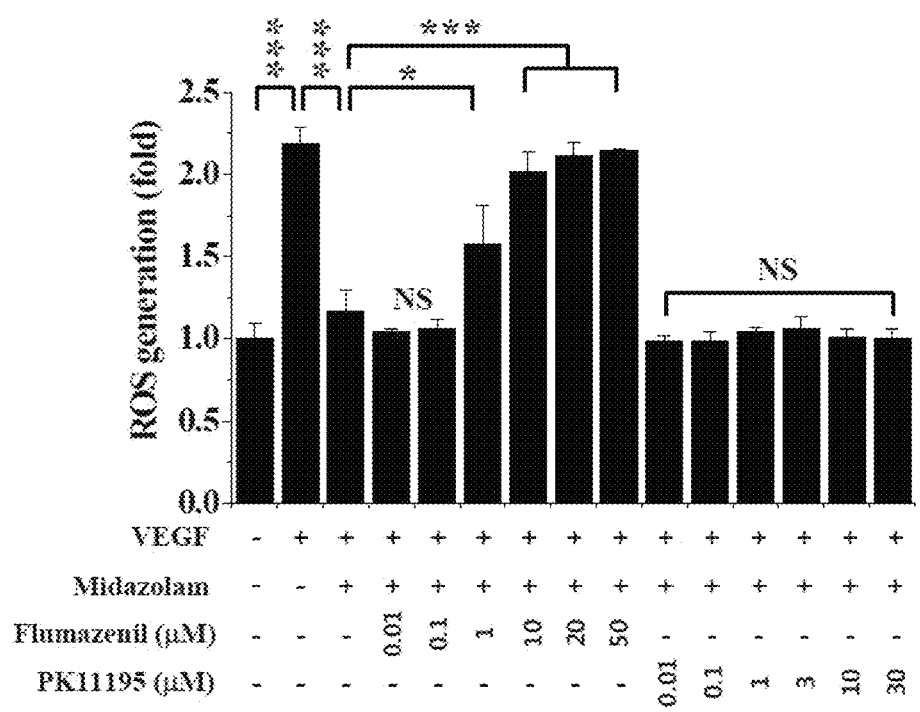

With reference to FIG. 10B, the HRECs of Test Example 1 were treated with 0 μM, 0.01 μM, 0.1 μM, 1 μM, 10 μM, 20 μM, and 50 μM flumazenil and 0 μM, 0.01 μM, 0.1 μM, 1 μM, 3 μM, 10 μM, and 30 μM PK11195, cultured for 1 hr, treated with 20 μM midazolam, cultured for 30 min, treated with 10 ng/ml VEGF, incubated for 10 min, treated with 10 μM H2DCFDA, stained for 10 min in a phenol-red-free low-serum medium, and then measured using confocal microscopy to thus determine the fluorescence intensity of single cells.

Based on the results of measurement, the flumazenil-treated HRECs exhibited an increase in ROS concentration with an increase in flumazenil concentration, whereas the PK11195-treated HRECs exhibited no increase in ROS concentration, regardless of the PK11195 concentration.

Accordingly, despite treatment with midazolam having the effect of suppressing ROS increase, ROS concentration was increased with an increase in the concentration of flumazenil serving as the $GABA_A$ receptor antagonist, from which midazolam can be found to act on the cells through the $GABA_A$ receptor.

Figure 11A:
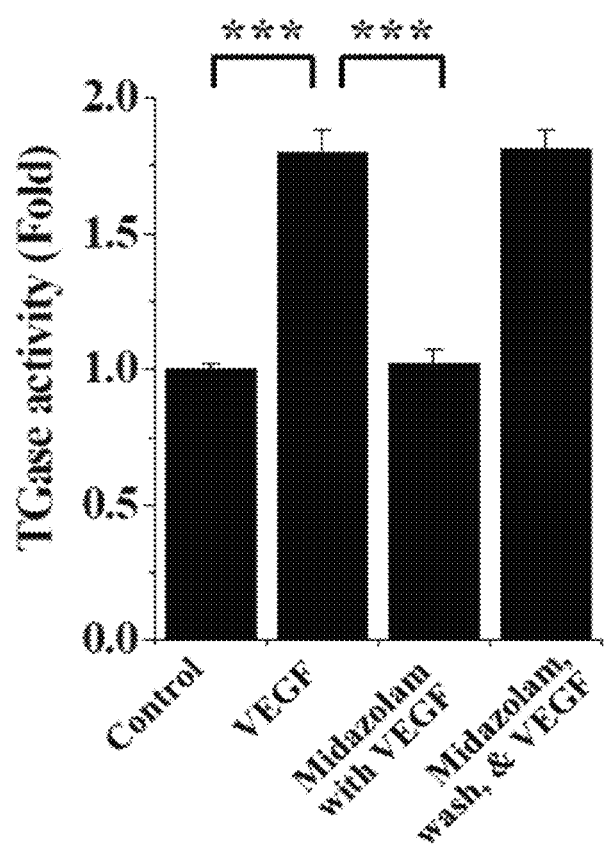
FIGS. 11A and 11B show the effects of flumazenil, serving as the $GABA_A$ receptor antagonist, and PK11195, serving as the TSPO receptor antagonist, on TGase activity increased by VEGF in Test Example 9 of the present invention.

Test Example 9. Identification of Receptor of Midazolam Through TGase Activity Analysis With reference to FIG. 11A, the HRECs of Test Example 1 were subjected to the respective treatments below, cultured for 2 hr, treated with 1 mM 5-(biotinamido)pentylamine, incubated for 1 hr, fixed with 3.7% formaldehyde, treated with 0.2% triton X-100, treated with a blocking solution containing 138 mM NaCl, 0.1% Tween 20 and 2% BSA dissolved in a 20 mM Tris (pH 7.6) buffer, incubated for 30 min, incubated with FITC-conjugated streptavidin (1:200, v/v) for 1 hr, and then measured using confocal microscopy to thus determine the fluorescence intensity of single cells.

i) Non-treatment (Control)
ii) Treatment with 10 ng/ml VEGF (VEGF)
iii) Treatment with 20 μM midazolam, culture for 10 min and treatment with 10 ng/ml VEGF (Midazolam with VEGF)
iv) Treatment with 20 μM midazolam, culture for 30 min, washing with serum-free medium and treatment with 10 ng/ml VEGF (Midazolam, wash, & VEGF)

Based on the results of measurement, compared to the i) non-treated HRECs (Control), no significant TGase activity increase was observed in the HRECs subjected to iii) treatment with midazolam and VEGF (Midazolam+VEGF), and TGase activity was increased in the HRECs subjected to ii) treatment with VEGF (VEGF) and the HRECs subjected to iv) treatment with midazolam, washing and treatment with VEGF (Midazolam, wash, & VEGF).

As will be described below, flumazenil was used as a $GABA_A$ receptor antagonist and PK11195 was used as a TSOP receptor antagonist.

Figure 11B:
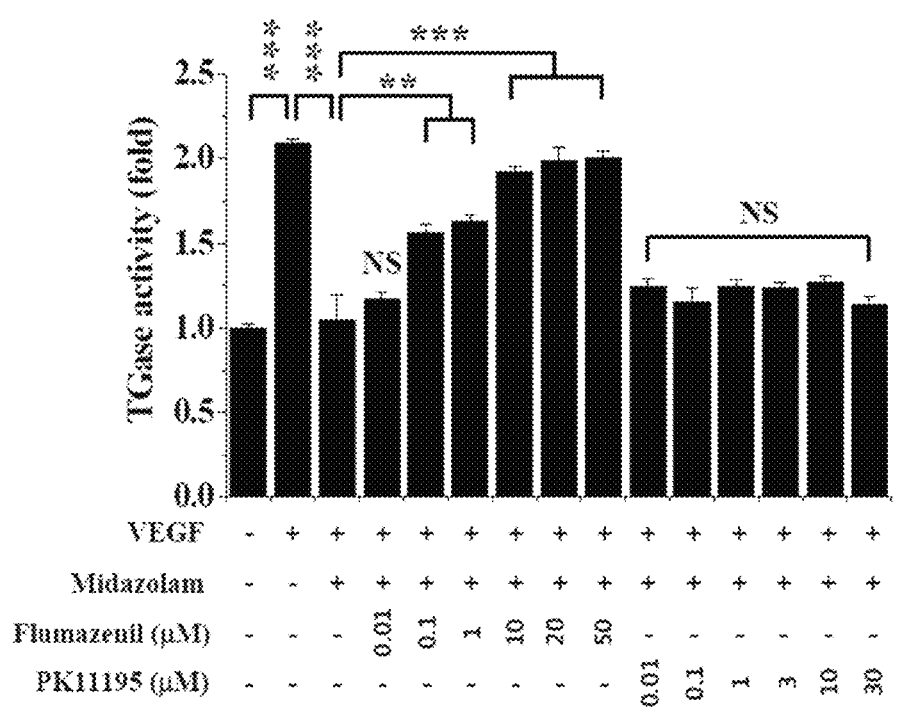

With reference to FIG. 11B, the HRECs of Test Example 1 were treated with 0 μM, 0.01 μM, 0.1 μM, 1 μM, 10 μM, 20 μM, and 50 μM flumazenil and 0 μM, 0.01 μM, 0.1 μM, 1 μM, 3 μM, 10 μM, and 30 μM PK11195, cultured for 1 hr, treated with 20 μM midazolam, cultured for 30 min, treated with 10 ng/ml VEGF, incubated for 10 min, treated with 1 mM 5-(biotinamido)pentylamine, incubated for 1 hr, fixed with 3.7% formaldehyde, treated with 0.2% triton X-100, treated with a blocking solution containing 138 mM NaCl, 0.1% Tween 20 and 2% BSA dissolved in a 20 mM Tris (pH 7.6) buffer, incubated for 30 min, incubated with FITC-conjugated streptavidin (1:200, v/v) for 1 hr, and then measured using confocal microscopy to thus determine the fluorescence intensity of single cells.

Based on the results of measurement, the flumazenil-treated HRECs exhibited an increase in TGase activity with an increase in flumazenil concentration, whereas the PK11195-treated HRECs exhibited no increase in TGase activity, regardless of the PK11195 concentration.

Accordingly, despite treatment with midazolam having the effect of suppressing TGase activation, TGase activity was increased with an increase in the concentration of flumazenil serving as the $GABA_A$ receptor antagonist, from which midazolam can be found to act on the cells through the $GABA_A$ receptor.

Test Example 10. Production of Diabetic Mouse Model 6-week-old male C57BL/6 mice (DBL, EumSeong, Korea) were administered with streptozotocin (Sigma-Aldrich) dissolved in a 100 mM citrate buffer (pH 4.5) through intraperitoneal injection in an amount of 150 mg each per kg of mouse weight to give diabetic mouse models. In the diabetic mouse models, the blood glucose level was 19 mM or more when not fasting, and polyuria and diabetes, considered signs of diabetes, were observed.

Test Example 11. Analysis of ROS Concentration in Mouse Model

Each of the diabetic mice was anesthetized with 2.5% avertin containing 250 mg of 2,2,2-tribromoethanol per kg thereof through intraperitoneal injection, after which 2 µL of 2 mM midazolam, 2 µL of 2 µM Trolox or 2 µL of 500 mM NAC was injected into the vitreous humor of one eye thereof, and the same volume (2 µL) of PBS was injected into the vitreous humor of the other eye thereof.

Figure 12:
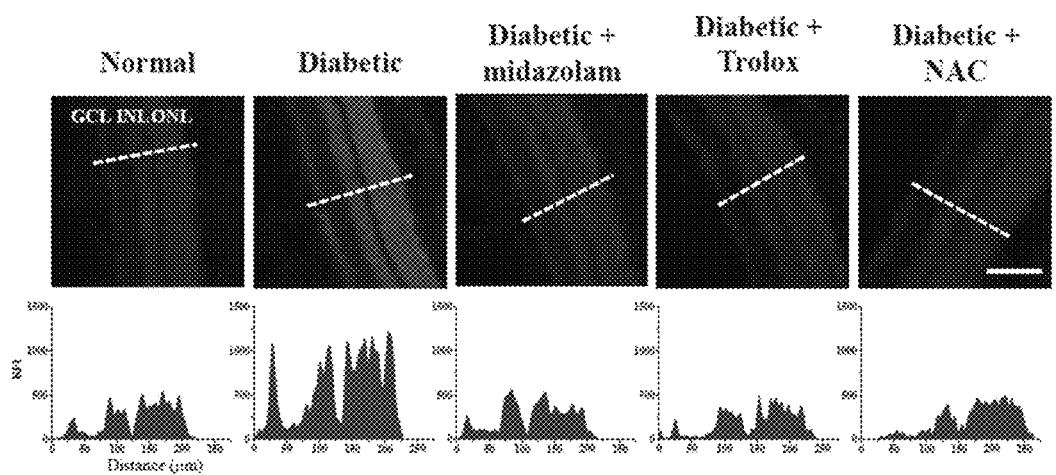
FIGS. 12 and 13 show the results of measurement of changes in ROS concentration in the retinas of the mouse models in Test Example 11 of the present invention.
Figure 13:
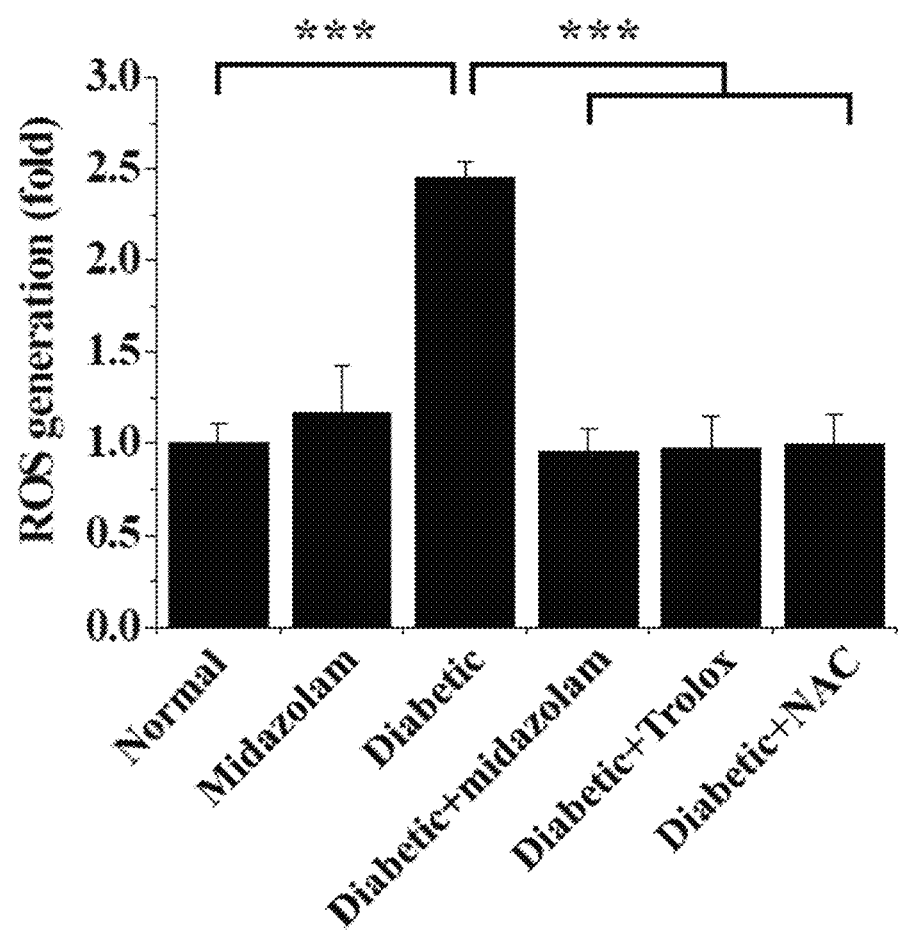

Normal mice (Normal), midazolam-administered normal mice (Midazolam), diabetic mice (Diabetic), midazolam-administered diabetic mice (Diabetic+Midazolam), Trolox-administered diabetic mice (Diabetic+Trolox) and NAC-administered diabetic mice (Diabetic+NAC) were subjected to cervical dislocation and the eyeballs were extracted therefrom and rapidly frozen with an OCT compound (Sakura Finetek, Torrance, Calif., USA). Using a microtome-cryostat (Leica Biosystems, Wetzlar, Germany), 10 µm-thick non-fixed cryosections were prepared, treated with a solution of 5 µM dihydroethidium (DHE, Invitrogen-Molecular Probes) in PBS, stained for 30 min, and measured using confocal microscopy. The results of ROS concentrations quantitatively analyzed using the fluorescence intensity of the cryosections are shown in FIGS. 12 and 13.

Based on the results of measurement, compared to the normal mice (Normal) as a control, no significant ROS concentration increase was observed in any of the test groups, excluding the diabetic mice (Diabetic), and thus the same results as in the cell testing (Test Example 3) were obtained.

That is, an increase in ROS concentration was suppressed because of the administration of midazolam.

Test Example 12. Analysis of TGase Activity in Mouse Model

Each of the diabetic mice was anesthetized with 2.5% avertin containing 250 mg of 2,2,2-tribromoethanol per kg thereof through intraperitoneal injection, after which 2 µL of 2 mM midazolam, 3 µL of 0.4 mM flumazenil in two administrations, and 2 µL of 2 mM midazolam, 2 of 2 µM cystamine or 2 µL of 500 mM MDC were injected into the vitreous humor of one eye thereof, and the same volume (2 µL) of PBS was injected into the vitreous humor of the other eye thereof.

Figure 14:
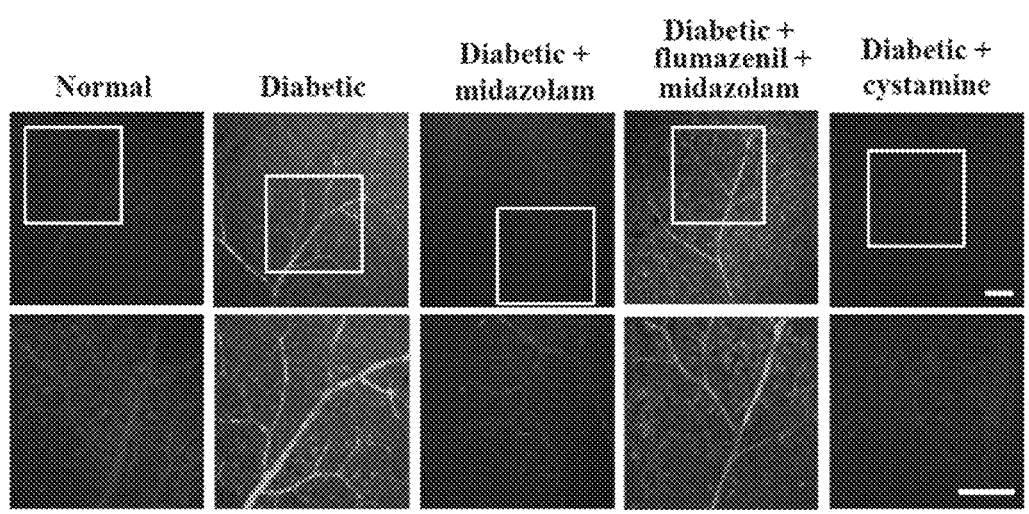
FIGS. 14 and 15 show the results of measurement of changes in TGase activity in the retinas of the mouse models in Test Example 12 of the present invention.
Figure 15:
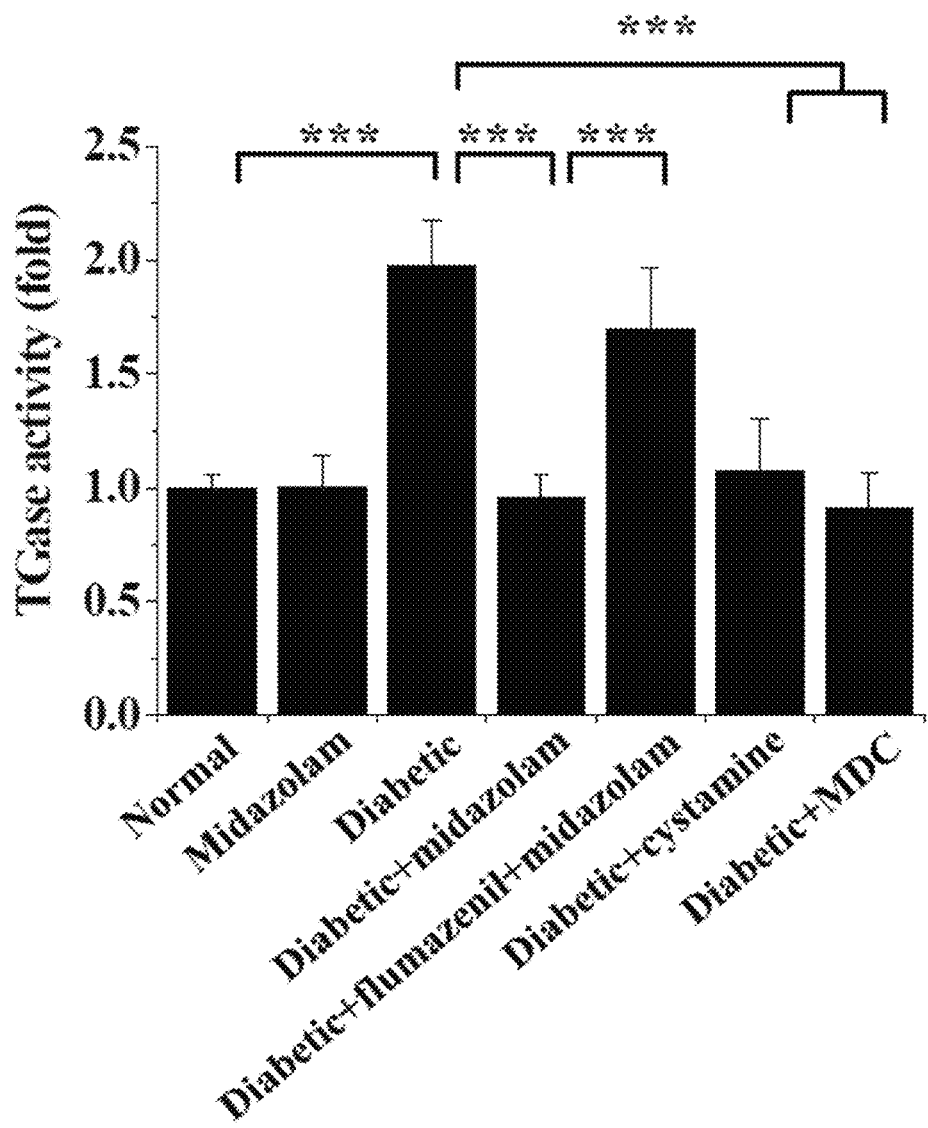

48 µL of 100 mM 5-(biotinamido)pentylamine was injected into the left ventricle of each of normal mice (Normal), midazolam-administered normal mice (Midazolam), diabetic mice (Diabetic), midazolam-administered diabetic mice (Diabetic+Midazolam), flumazenil- and midazolam-administered diabetic mice (Diabetic+flumazenil+Midazolam), cystamine-administered diabetic mice (Diabetic+cystamine) and MDC-administered diabetic mice (Diabetic+MDC) and circulated for 10 min, after which cervical dislocation was performed, and the eyeballs were extracted, fixed with 4% paraformaldehyde for 45 min, incised and subjected to permeation treatment for 30 min. The obtained retinal samples were incubated with a blocking solution for 30 min, treated with FITC-conjugated streptavidin (1:200, v/v), and stained for 1 hr, and measured using confocal microscopy. The results of TGase activity quantitatively analyzed using the fluorescence intensity of the retinal samples are shown in FIGS. 14 and 15.

Based on the results of measurement, compared to the normal mice (Normal) as a control, no significant TGase activity increase was observed in any of the test groups, excluding the diabetic mice (Diabetic) and the flumazenil- and midazolam-administered diabetic mice (Diabetic+flumazenil+Midazolam), and thus the same results as in the cell testing (Test Examples 4 and 9) were obtained.

That is, an increase in TGase activation was suppressed because of the administration of midazolam. Here, midazolam can be confirmed to act on the cells through the $GABA_A$ receptor.

Test Example 13. Fluorescein Angiography for Mouse Model

Each of the diabetic mice was anesthetized with 2.5% avertin containing 250 mg of 2,2,2-tribromoethanol per kg thereof through intraperitoneal injection, and 2 µL of 2 mM midazolam, 3 µL of 0.4 mM flumazenil in two administrations, and 2 µL of 2 mM midazolam, 2 of 2 µM cystamine or 2 µL of 500 mM MDC were injected into the vitreous humor of one eye thereof, and the same volume (2 µL) of PBS was injected into the vitreous humor of the other eye thereof.

Figure 16:
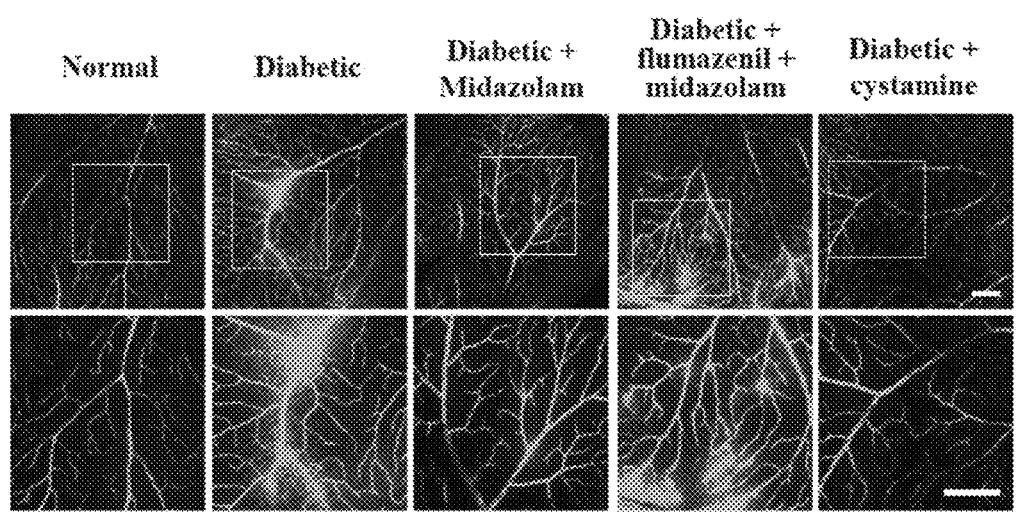
FIGS. 16 and 17 show the results of measurement of vascular leakage in the retinas of the mouse models in Test Example 13 of the present invention.
Figure 17:
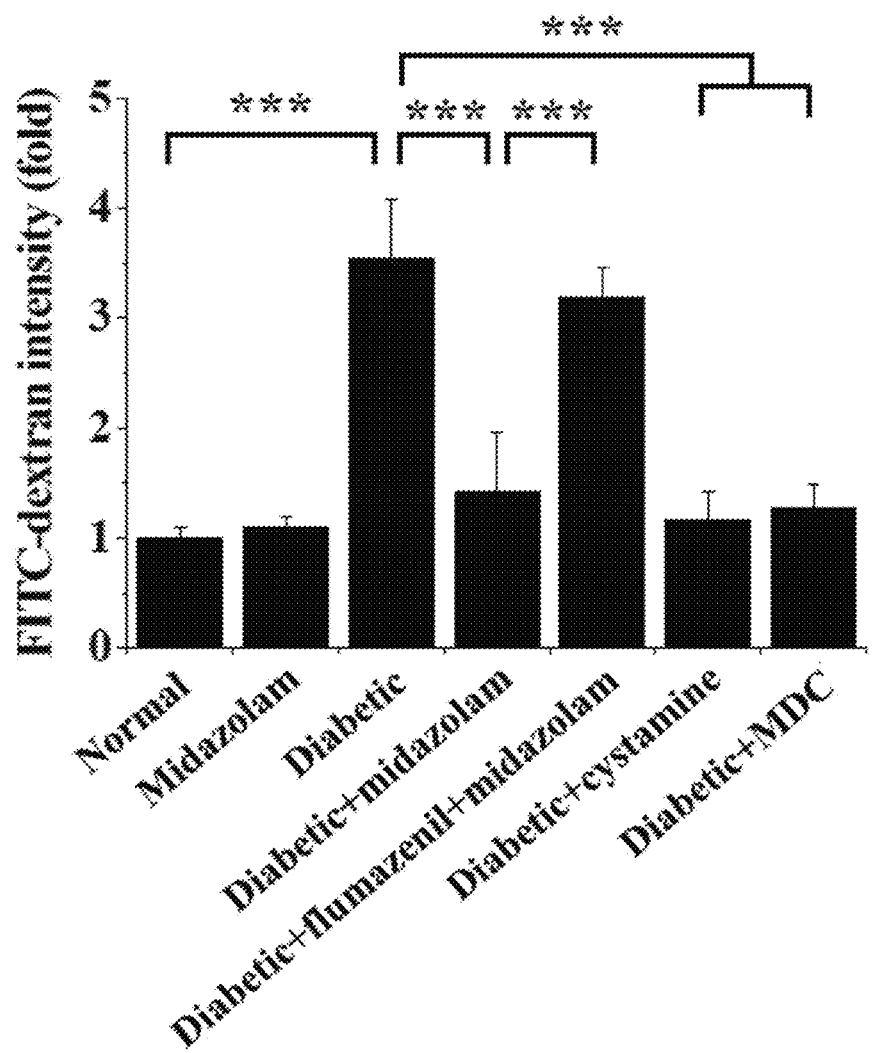

48 µL of 100 mM 5-(biotinamido)pentylamine was injected into the left ventricle of each of normal mice (Normal), midazolam-administered normal mice (Midazolam), diabetic mice (Diabetic), midazolam-administered diabetic mice (Diabetic+Midazolam), flumazenil- and midazolam-administered diabetic mice (Diabetic+flumazenil+Midazolam), cystamine-administered diabetic mice (Diabetic+cystamine) and MDC-administered diabetic mice (Diabetic+MDC) and circulated for 10 min, after which cervical dislocation was performed and the eyeballs were extracted, fixed with 4% paraformaldehyde for 45 min, incised and subjected to permeation treatment for 30 min. The obtained retinal samples were incubated with a blocking solution for 30 min, treated with FITC-conjugated streptavidin (1:200, v/v), and stained for 1 hr, and the retinal surface vessels thereof were measured using confocal microscopy. The results of quantitative analysis by measuring the fluorescence intensity emitted to the outside from the retinal vessels due to vascular leakage are shown in FIGS. 16 and 17.

Based on the results of measurement, compared to the normal mice (Normal) as a control, no significant TGase activity increase was observed in any of the test groups, excluding the diabetic mice (Diabetic) and the flumazenil- and midazolam-administered diabetic mice (Diabetic+flumazenil+Midazolam), and thus the same results as in the cell testing were obtained.

That is, vascular leakage was prevented because of the administration of midazolam. Here, midazolam can be confirmed to act on the cells through the $GABA_A$ receptor.

Test Example 14. Identification of $GABA_A$ Receptor in Mouse Model

Each of the normal mice was subjected to cervical dislocation and the eyeballs were extracted therefrom, fixed with 4% paraformaldehyde for 45 min, incised and subjected to permeation treatment for 30 min, and the retinal samples were incubated in a blocking solution for 30 min. The retinal samples were incubated with a polyclonal $GABA_A$ receptor α1 antibody (1:200; Abcam) at 4° C. for 12 hr or more, treated with a FITC-conjugated goat anti-rabbit antibody (Sigma-Aldrich), incubated for 2 hr, treated with isolectin B4 (1:1000; Invitrogen), stained for 2 hr, and measured using confocal microscopy. The results are shown in FIG. 18A.

Each of the normal mice was subjected to cervical dislocation and the eyeballs were extracted therefrom, fixed with 4% paraformaldehyde for 12 hr or more, treated with 30% sucrose at 4° C. for 12 hr or more, and frozen, and the 10 μm-thick retinal cryosections were subjected to permeation treatment and then incubated with a blocking solution. The retinal sections were incubated with a polyclonal $GABA_A$ receptor al antibody (1:200; Abcam) for 12 hr or more, treated with a FITC-conjugated goat anti-rabbit antibody (Sigma-Aldrich) and 1 μg/ml DAPI (4',6-diamidine-2'-phenylindole dihydrochloride, Abcam), stained for 10 min, and measured using confocal microscopy. The results are shown in FIG. 18B.

Figure 18A:
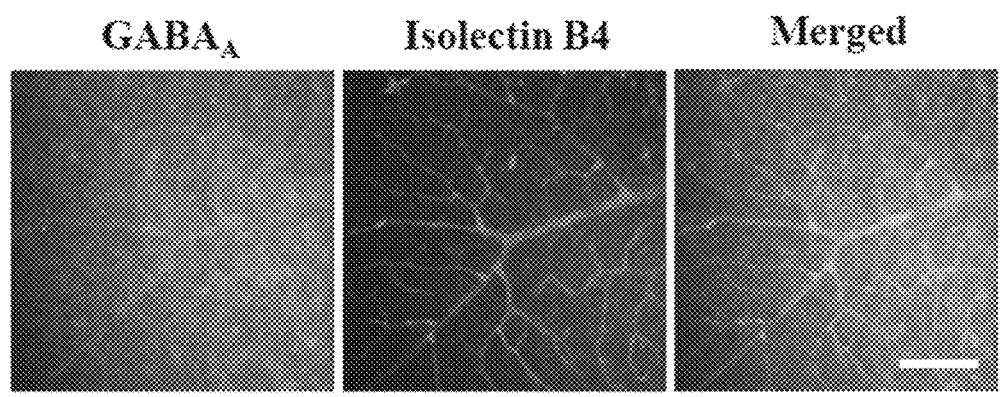
FIGS. 18A and 18B show the position of the $GABA_A$ receptor in the retinas of the mouse models in Test Example 14 of the present invention.
Figure 18B:
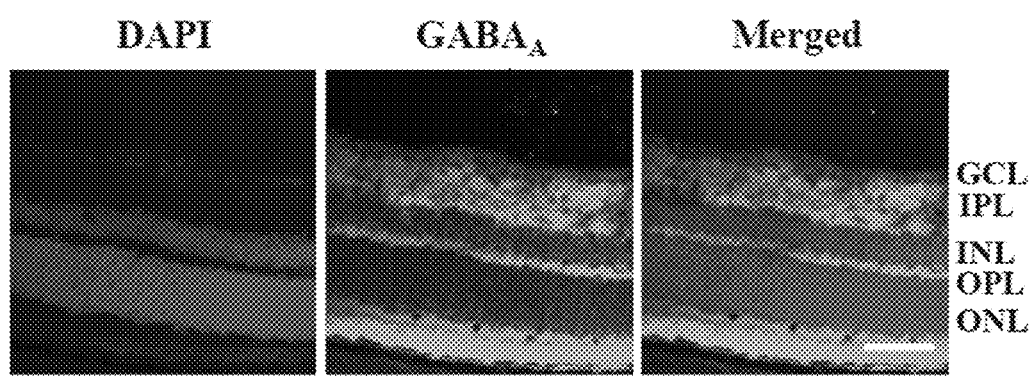

Based on the results of measurement, as shown in FIG. 18A, the $GABA_A$ receptor was positioned in the retinal vessels and ganglion cells, and as shown in FIG. 18B, the $GABA_A$ receptor was positioned in the retinal cell layers, especially the ganglion cell layer (GCL), the inner plexiform layer (INL) and the outer nuclear layer (ONL).

Test Example 15. Midazolam Treatment of Diabetic Cardiovascular Disease

Figure 19A:
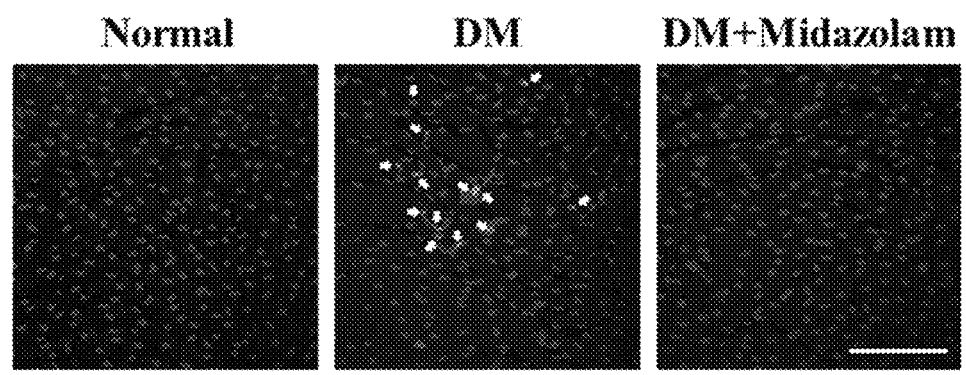
FIG. 19A are confocal micrographic images of endothelial apoptosis in normal cells, diabetic cells and treated diabetic cells in accordance with an embodiment of the invention.
Figure 19B:
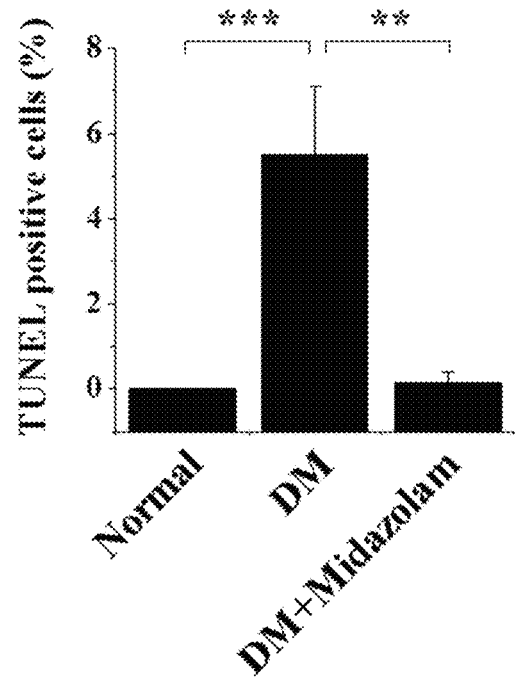
FIG. 19B is a bar graph showing quantitative analysis of endothelial apoptosis in normal cells, diabetic cells and treated diabetic cells in accordance with an embodiment of the invention.

FIGS. 19A and 19B show the preventive effects of midazolam against hyperglycemia-induced endothelial apoptosis in the aortic endothelium of diabetic mice. Six-week-old male C57BL/6 mice were administered with streptozotocin (150 mg/kg body weight) to give diabetic mouse models. One week after streptozotocin injection, diabetic mice were administered midazolam (10 mg/kg) by intraperitoneal injection daily for 14 days. The body weight of mice were measure in normal (20.7±0.1 g), diabetic (17.1±0.1 g), and midazolam supplemented diabetic mice (17.0±0.3 g). Blood glucose levels were also monitored in normal (124.0±12.0 mg/dL), diabetic (509.0±1.0 mg/dL), and midazolam supplemented diabetic mice (515.7±3.4 mg/dL). Aorta of mice were dissected and cut longitudinally to expose the endothelium. And then aortic segments were fixed for 15 min with 1% (w/v) paraformaldehyde in PBS, followed by treatment for 30 min with 70% (v/v) ethanol on ice. Apoptotic cells were stained by terminal deoxynucleotidyl transferase dUTP nick end labeling (TUNEL) with nuclear counterstaining with DAPI and visualized by confocal microscopy in the aortic endothelium. Representative images of endothelial apoptosis in aorta are shown in additional FIG. 19A. Scale bar, 100 μm. The results of endothelial apoptosis quantitatively analyzed by measurement of TUNEL staining in the aorta are shown in additional FIG. 19B (n=4 for normal and diabetic, n=6 for diabetic+Midazolam).

Base on the results of measurement, high glucose increased endothelial apoptosis in diabetic mice. However, midazolam inhibited the hyperglycemia-induced apoptosis of diabetic aortas, assessed by TUNEL staining That is, midazolam prevents against hyperglycemia-induced endothelial apoptosis in the aorta of diabetic mice. Here, midazolam can be confirmed to act on the aorta of diabetic mice.

Test Example 16. Midazolam Treatment of Diabetic Kidney Disease

Figure 20A:
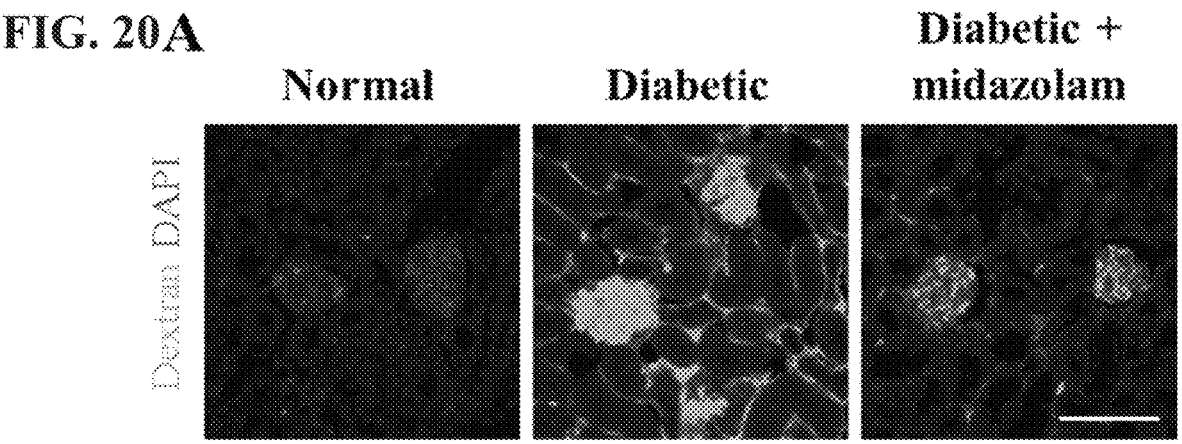
FIG. 20A are confocal micrographic images of vascular leakage in normal kidney cells, diabetic kidney cells and treated diabetic kidney cells in accordance with an embodiment of the invention.
Figure 20B:
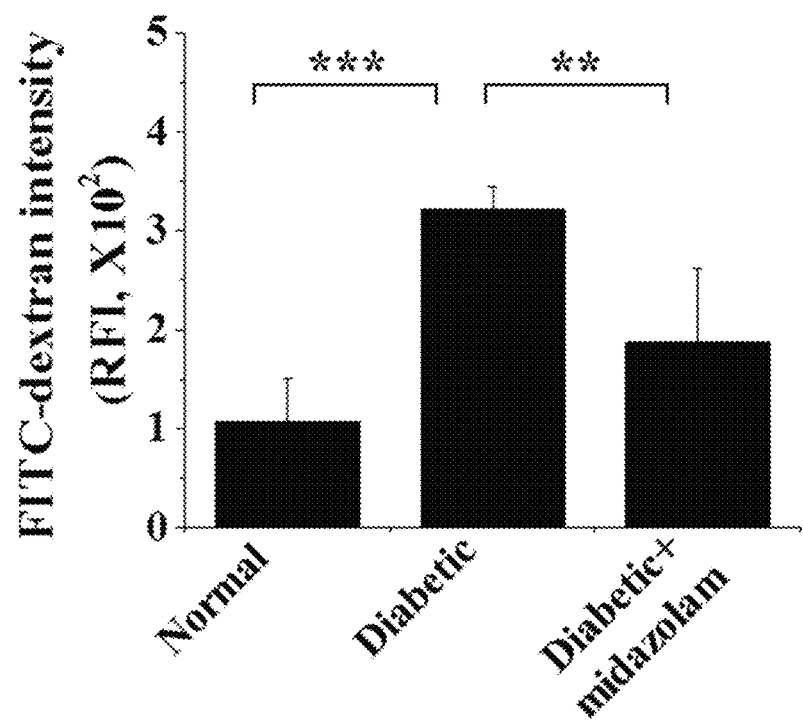
FIG. 20B is a bar graph showing quantitative analysis of vascular leakage in normal kidney cells, diabetic kidney cells and treated diabetic kidney cells in accordance with an embodiment of the invention.

FIGS. 20A and 20B show the preventive effects of midazolam against hyperglycemia-induced renal vascular leakage in diabetic mice. Six-week-old male C57BL/6 mice were administered with streptozotocin (150 mg/kg body weight) to give diabetic mouse models. Two weeks after streptozotocin injection, diabetic mice were administered 10 mg/kg midazolam by intraperitoneal injection daily for 2 days, and vascular leakage was investigated. The body weight of mice were measure in normal (19.9±0.3 g), diabetic (17.7±0.3 g), and midazolam supplemented diabetic mice (17.7±0.3 g). Blood glucose levels were also monitored in normal (123.5±6.5 mg/dL), diabetic (505.0±89.0 mg/dL), and midazolam supplemented diabetic mice (500.3±63.3 mg/dL). The mice were anesthetized with 3% isoflurane, and 1.25 mg of FITC-dextran was injected into the right ventricle of each mouse and allowed to circulate for 5 min. The kidneys were dissected, fixed, and embedded in OCT compound. Cryosections of kidneys were stained with nuclear counterstaining with DAPI. Representative images of vascular leakage in kidneys are shown in additional FIG. 20A. Scale bars, 100 μm. The results of vascular leakage quantitatively analyzed by measuring the fluorescence intensity of FITC-dextran in the kidneys are shown in additional FIG. 20B. (n=4 for normal and diabetic, n=6 for diabetic+Midazolam).

Base on the results of measurement, VEGF-induced vascular leakage in mouse ear was suppressed at 10 mg/kg midazolam but not at 5 mg/kg. Renal vascular leakage in the kidneys was observed as higher levels of FITC-dextran extravasation in diabetic mice than in normal controls, and it was blocked by midazolam administration (n=4 for normal and diabetic, n=6 for diabetic+Midazolam). That is, renal vascular leakage was prevented because of the administration of midazolam. Here, midazolam can be confirmed to act on the kidneys of diabetic mice.

Test Example 17. Midazolam Treatment of Diabetic Lung Disease

Figure 21A:
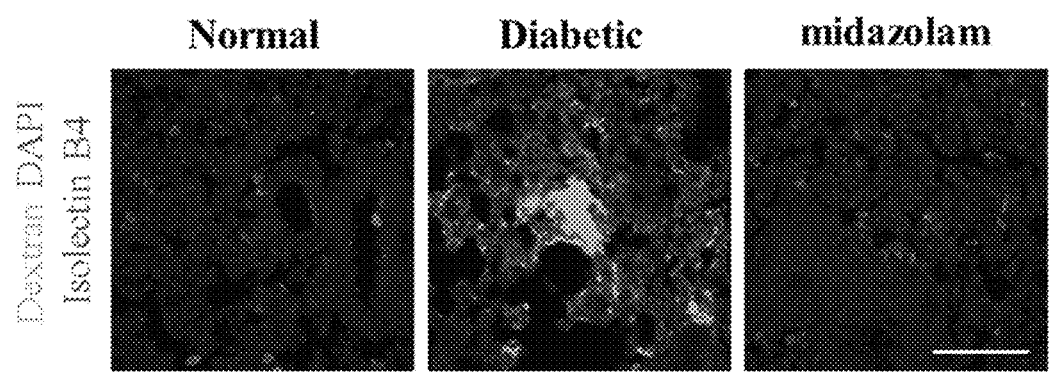
FIG. 21A are confocal micrographic images of vascular leakage in normal lung cells, diabetic lung cells and treated diabetic lung cells in accordance with an embodiment of the invention.
Figure 21B:
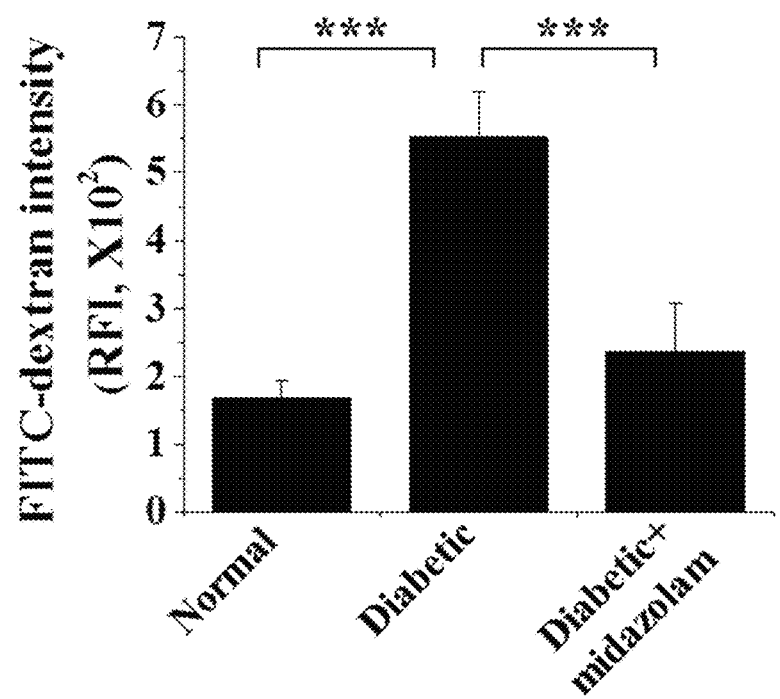
FIG. 21B is a bar graph showing quantitative analysis of vascular leakage in normal lung cells, diabetic lung cells and treated lung kidney cells in accordance with an embodiment of the invention.

FIGS. 21A and 21B show the preventive effects of midazolam against hyperglycemia-induced pulmonary vascular leakage in diabetic mice. Six-week-old male C57BL/6 mice were administered with streptozotocin (150 mg/kg body weight) to give diabetic mouse models. Two weeks after streptozotocin injection, diabetic mice were administered 10 mg/kg midazolam by intraperitoneal injection daily for 2 days, and vascular leakage was investigated. The body weight of mice were measure in normal (19.9±0.3 g), diabetic (17.7±0.3 g), and midazolam supplemented diabetic mice (17.6±0.3 g). Blood glucose levels were also monitored in normal (123.5±6.5 mg/dL), diabetic (505.0±89.0 mg/dL), and midazolam supplemented diabetic mice (500.3±63.3 mg/dL). The mice were anesthetized with 3% isoflurane, and 1.25 mg of FITC-dextran was injected into the right ventricle of each mouse and allowed to circulate for 5 min. The lungs were dissected, fixed, and embedded in OCT compound. Cryosections of lungs were stained with isolectin B4 and DAPI. Representative images of vascular leakage in lungs are shown in additional FIG. 21A. Scale bars, 100 μm. The results of vascular leakage quantitatively analyzed by measuring the fluorescence intensity of FITC-dextran in the lungs are shown in additional FIG. 21B (n=4 for normal and diabetic, n=6 for diabetic+Midazolam).

Base on the results of measurement, pulmonary vascular leakage in the lungs was observed as higher levels of FITC-dextran extravasation in diabetic mice than in normal controls, and it was blocked by midazolam administration. That is, increase in pulmonary vascular leakage was prevented because of the administration of midazolam. Here, midazolam can be confirmed to act on the lungs of diabetic mice.

Test Example 18. Midazolam Treatment of Diabetic Cancer Metastasis

Figure 22:
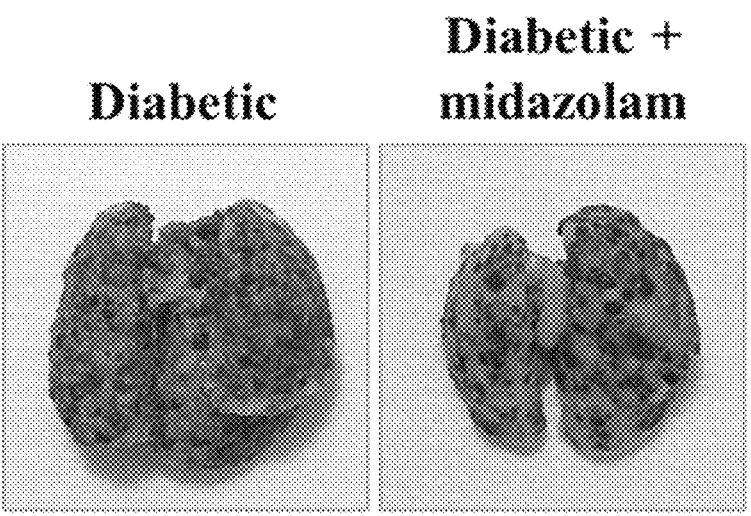
FIG. 22A are images of a hyperglycemic-induced tumor and a treated hyperglycemic-induced tumor in accordance with an embodiment of the invention.
FIG. 22B is a bar graph showing the number of metastatic nodules in hyperglycemic-induced tumors and treated hyperglycemic-induced tumors in accordance with an embodiment of the invention.
Figure 22:
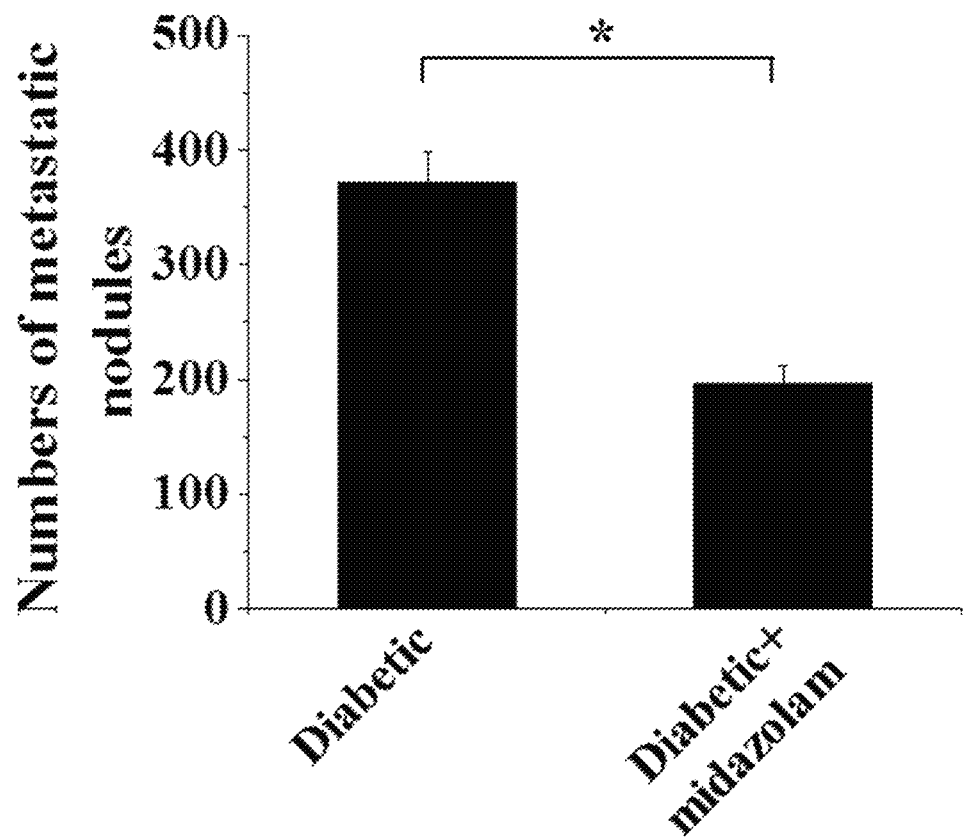

FIGS. 22A and 22B show the preventive effects of midazolam against hyperglycemia-induced cancer metastasis in the lungs of diabetic mice. Six-week-old male C57BL/6 mice were administered with streptozotocin (150 mg/kg) to give diabetic mouse models. One weeks after streptozotocin injection, diabetic mice were administered 10 mg/kg midazolam by intraperitoneal injection daily for 14 days, and diabetic and midazolam supplemented diabetic mice were intravenously injected with B16F10 cells ($5 \times 10^5$) in PBS. The weight of mice were measure in diabetic (16.4±0.2 g) and midazolam supplemented diabetic mice (16.2±0.5 g). Blood glucose levels were also monitored in diabetic (511.0±10.0 mg/dL) and midazolam supplemented diabetic mice (515.7±3.4 mg/dL). Two weeks later, the mice were euthanized by cervical dislocation, and the lungs were removed and bleached in Fekete's solution (70% ethanol, 3.7% paraformaldehyde, 0.75 M glacial acetic acid). Representative images of melanoma metastasis in lungs are shown in additional FIG. 22A. The results of melanoma metastasis assessed by counting metastatic lung nodules under a dissection microscope are shown in additional FIG. 22B (n=2/group).

Base on the results of measurement, the number of metastatic nodules in the lungs of diabetic mice was suppressed by midazolam administration in diabetic mice. That is, cancer metastasis in the diabetic mice was prevented because of the administration of midazolam. Here, midazolam can be confirmed to act on the cancer metastasis of diabetic mice.

Test Example 19. Midazolam Treatment of VEGF-Induced Vascular Leakage

Figure 23:
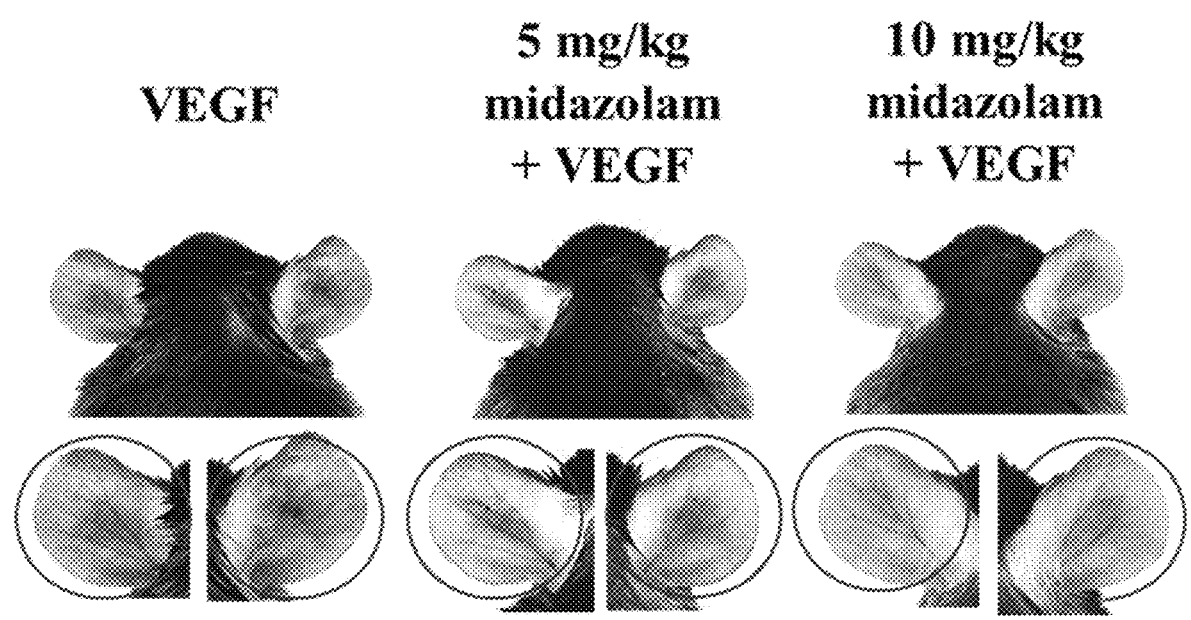
FIG. 23 are images of VEGF-induced vascular leakage in mice following different treatments in accordance with an embodiment of the invention.

FIG. 23 shows the preventive effects of midazolam against VEGF-induced vascular leakage in ears of diabetic mice. Six-week-old male C57BL/6 mice were administered 5 or 10 mg/kg midazolam by intraperitoneal injection. After 24 hr, mice were intravenously injected with 45 mg/kg evans blue dye. After 30 min circulation, 10 µl VEGF solution (30 ng) was injected intradermally into the dorsal part of ears. Representative images of vascular leakage in ears are shown in additional FIG. 23 (n=2/group).

Base on the results of measurement, VEGF-induced vascular leakage in mouse ear was suppressed at 10 mg/kg midazolam but not at 5 mg/kg. That is, VEGF-induced vascular leakage was prevented because of the administration of midazolam and this prevention showed a dose response to different amounts of midazolam administered. Here, midazolam can inhibit diabetic complications caused by hyperglycemia-induced vascular leakage, including diabetic retinopathy, lung disease, cancer metastasis, and kidney disease.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for prevention or treatment of diabetic complications caused by hyperglycemia-induced vascular leakage, comprising administering an effective amount of a benzodiazepine-based compound to an animal in need thereof
wherein the diabetic complications caused by hyperglycemia-induced vascular leakage is selected from the group consisting of diabetic retinopathy, diabetic cardiovascular disease, diabetic lung disease, kidney disease, and diabetic cancer metastasis and wherein said benzodiazepine-based compound is midazolam.

2. The method of claim 1, wherein the vascular leakage is caused by a vascular endothelial growth factor (VEGF).

3. The method of claim 2, wherein the benzodiazepine-based compound inhibits intracellular $Ca^{2+}$ elevation induced by the VEGF.

4. The method of claim 3, wherein the benzodiazepine-based compound inhibits at least one of reactive oxygen species (ROS) generation, transglutaminase (TGase) activation and adherens junction disruption, which are induced by the intracellular $Ca^{2+}$ elevation.

5. The method of claim 1, wherein the benzodiazepine-based compound acts through a γ-aminobutyric acid type A ($GABA_A$) receptor.

6. The method of claim 1, wherein the administering of a benzodiazepine-based compound includes at least one selected from among ocular administration, intravitreal injection, vascular injection, intraperitoneal injection, subcutaneous injection, nasal aspiration and oral administration.

7. The method of claim 1, wherein the animal is a human.

8. A method of reducing vascular leakage in a patient suffering from diabetes comprising administering an effective amount of a benzodiazepine-based compound and wherein said benzodiazepine-based compound is midazolam.

9. The method of claim 8, wherein the benzodiazepine-based compound acts through a γ-aminobutyric acid type A ($GABA_A$) receptor.

10. The method of claim 8, wherein the vascular leakage is caused by a vascular endothelial growth factor (VEGF).

11. The method of claim 10, wherein the benzodiazepine-based compound inhibits intracellular $Ca^{2+}$ elevation induced by the VEGF.

12. The method of claim 8, wherein the vascular leakage is hyperglycemia-induced.

13. The method of claim 8, wherein the patient has diabetic retinopathy, diabetic cardiovascular disease, diabetic lung disease, kidney disease, and/or diabetic cancer metastasis.

14. The method of claim 8, wherein the method inhibits at least one of reactive oxygen species (ROS) generation, transglutaminase (TGase) activation and adherens junction disruption, which are induced by the intracellular $Ca^{2+}$ elevation.

15. The method of claim 8, wherein the method comprises administering at least 10 mg/kg of the benzodiazepine-based compound.

* * * * *